(12) United States Patent
Ott

(10) Patent No.: US 8,222,299 B2
(45) Date of Patent: *Jul. 17, 2012

(54) ORGANOSULFUR PRODRUGS FOR THE PREVENTION AND TREATMENT OF INFECTIOUS DISEASES

(75) Inventor: David M. Ott, Oakland, CA (US)

(73) Assignee: Allium Vitalis Incorporated, Berkeley, CA (US)

( * ) Notice: Subject to any disclaimer, the term of this patent is extended or adjusted under 35 U.S.C. 154(b) by 759 days.

This patent is subject to a terminal disclaimer.

(21) Appl. No.: 10/853,415

(22) Filed: May 24, 2004

(65) Prior Publication Data

US 2004/0235946 A1 Nov. 25, 2004

Related U.S. Application Data

(60) Provisional application No. 60/472,791, filed on May 23, 2003.

(51) Int. Cl.
*A61K 31/095* (2006.01)
(52) U.S. Cl. ...................................................... 514/706
(58) Field of Classification Search .................. None
See application file for complete search history.

(56) References Cited

U.S. PATENT DOCUMENTS

| | | | |
|---|---|---|---|
| 2,508,745 A | 5/1950 | Cavallito et al. | |
| 5,451,412 A | 9/1995 | Bounous et al. | |
| 2005/0260250 A1 | 11/2005 | Ott | |
| 2006/0269488 A1 | 11/2006 | Ott | |

FOREIGN PATENT DOCUMENTS

WO WO 01/367561 * 5/2001

OTHER PUBLICATIONS

Borek C. "Antioxidant Health Effects of Aged Garlic Extract", Mar. 2001, J. Nutr. vol. 131, pp. 1010S-1015S.*
Amagase H. et al. "Intake of Garlic and Its Bioactive Components", Mar. 2001, J. Nutr. vol. 131, pp. 955S-962S.*
Rabinkov A. et al. "The Mode of Action of Allicin: Trapping of Radicals and Interaction with Thiol Containing Proteins", 1998, Biochimica et Biophysica Acta vol. 1379, pp. 233-244.*
Mayo Clinic, Acute Respiratory Distress Syndrome, www.mayoclinic.com/health/ards/DS00944, Apr. 20, 2007.*
Mayo Clinic, Severe acute respiratory syndrome, www.mayoclinic.com/health/sars/DS00501, Jan. 6, 2009.*
Mayo Clinic, pneumonia, .mayoclinic.com/health/pneumonia/DS00135, May 10, 2007.*
Ali et al. "Garlic and onions: their effect on eicosanoid metabolism and its clinical relevance," Prostaglandins, Leukotrienes and Essential Fatty Acids, 2000, 62, 55-73.*
Morioka et al. "A protein fraction from aged garlic extract enhances cytotoxicity and proliferation of human lymphocytes mediated by interleukin-2 and concanavalin A," Cancer Immunol Immunother, 1993, 37, 316-22.*

Wakunaga of America Co. LTD. product label for KYOLIC® Aged Garlic ExtractTM Formula 100, 1999.*
"Classification of Garlic Products on the Market," www.kyolic.com, 2010.*
Patrick et al. "Sulfhydryl and Disulfide Groups in Skim Milk as Affected by Direct Ultra-High-Temperature Heating and Subsequent Storage," J. Dairy Science, 1976, 59, 594-600, abstract only.*
"N-acetylcysteine" in Alternative Medicine Review, 2000, 5, 467-471.*
Dirsch et al., "Effect of allicin and ajoene, two compounds of garlic, on inducible nitric oxide synthase", Atherosclerosis. Aug. 1998;139(2):333-9.
Mayeux et al., "The pharmacological effects of allicin, a constituent of garlic oil", Agents Actions. Aug. 1988;25 (1-2):182-90.
Powers et al., "Selective inhibition of functional lymphocyte subpopulations by ribavirin", Antimicrob Agents Chemother. Jul. 1982;22(1):108-14.
Tada et al., "Nematicidal and antimicrobial constituents from Allium grayi Regel and Allium fistulosum L. var. caespitosum", Agric. Biol. Chem. 1988 52(9), 2383-2385.
Josling, "Preventing the common cold with a garlic supplement: a double-blind, placebo-controlled survey", Adv Ther. Jul.-Aug. 2001;18(4):189-93.
Buono et al., "Total sulfur amino acid requirement in young men as determined by indicator amino acid oxidation with L-[1-13C]phenylalanine", Am J Clin Nutr. Dec. 2001;74(6):756-60.
Droge et al., "Modulation of lymphocyte functions and immune responses by cysteine and cysteine derivatives", Am J Med. Sep. 30, 1991;91(3C):140S-144S.
Morris et al., "Significance of glutathione in lung disease and implications for therapy", Am J Med Sci. Feb. 1994;307 (2):119-27.
Fallon et al., "Garlic prevents hypoxic pulmonary hypertension in rats", Am J Physiol. Aug. 1998;275(2 Pt 1):L283-7.
Leff et al., "Postinsult treatment with N-acetyl-L-cysteine decreases IL-1-induced neutrophil influx and lung leak in rats", Am J Physiol. Nov. 1993;265(5 Pt 1):L501-6.
Knight et al., "Acid aspiration increases sensitivity to increased ambient oxygen concentrations", Am J Physiol Lung Cell Mol Physiol. Jun. 2000;278(6):L1240-7.
Johnson et al., "Death of Salmonella typhimurium and Escherichia coli in the presence of freshly reconstituted dehydrated garlic and onion", Appl Microbiol. Jun. 1969;17(6):903-5.

(Continued)

*Primary Examiner* — Christina Bradley

(57) ABSTRACT

A method for enhancing the overall beneficial immune system response in a host that works in conjunction with the host's natural immune system response to simultaneously enhance the host's ability to eliminate infectious microbes while suppressing the toxicity of the immune system response to the host. Allium related organosulfur compounds have a variety of antimicrobial and immunomodulatory properties that work together with the host's immune system in the prevention and treatment of disease. Prophylactic and therapeutic treatment is provided by administering an allium related organosulfur compound such that a localized thiosulfinate is caused to be formed in response to localized generation of reactive oxygen species such as hydrogen peroxide by the activated immune system cells. Allium related organosulfur compounds may be administered to the host in an efficient manner through the use of protein-bound S-AllylMercapto-Cysteine or similar prodrugs.

21 Claims, 6 Drawing Sheets

OTHER PUBLICATIONS

Meister et al., "Glutathione", Annu Rev Biochem. 1983;52:711-60.
Iravani et al., "N-Acetylcysteine and mucociliary activity in mammalian airways", Arzneimittelforschung. 1978;28(2):250-4.
Rabinkov et al., "The mode of action of allicin: trapping of radicals and interaction with thiol containing proteins", Biochim Biophys Acta. Feb. 2, 1998;1379(2):233-44.
Miron et al., "The mode of action of allicin: its ready permeability through phospholipid membranes may contribute to its biological activity", Biochim Biophys Acta. Jan. 15, 2000;1463(1):20-30.
Wills, "Enzyme inhibition by allicin, the active principle of garlic", The Biochemical Journal. 1956 63:514-520.
Hayden et al., "Is type 2 diabetes mellitus a vascular disease (atheroscleropathy) with hyperglycemia a late manifestation? The role of NOS, NO, and redox stress", Cardiovasc Diabetol. Feb. 12, 2003;2:2.
Meduri et al., "Plasma and BAL cytokine response to corticosteroid rescue treatment in late ARDS", Chest. Nov. 1995;108(5):1315-25.
"Why does lactic acidosis occur in acute lung injury", Chest. May 1997;111(5):1157-8.
Kellum et al., "Release of lactate by the lung in acute lung injury", Chest. May 1997;111(5):1301-5.
Headley et al., "Infections and the inflammatory response in acute respiratory distress syndrome", Chest. May 1997;111(5):1306-21.
Bernard et al.,"A trial of antioxidants N-acetylcysteine and procysteine in ARDS. The Antioxidant in ARDS Study Group", Chest. Jul. 1997;112(1):164-72.
Kokura et al., "Molecular mechanisms of neutrophil-endothelial cell adhesion induced by redox imbalance", Circ Res. Mar. 19, 1999;84(5):516-24.
Lee et al., "Neutrophil activation and acute lung injury", Curr Opin Crit Care. Feb. 2001;7(1):1-7.
Shirin et al., "Antiproliferative effects of S-allylmercaptocysteine on colon cancer cells when tested alone or in combination with sulindac sulfide",Cancer Res. Jan. 15, 2001;61(2):725-31.
Teyssier et al., "Metabolism of diallyl disulfide by human liver microsomal cytochromes P-450 and flavin-containing monooxygenases", Drug Metab Dispos. Jul. 1999;27(7):835-41.
Sumioka et al., "Therapeutic effect of S-allylmercaptocysteine on acetaminophen-induced liver injury in mice", Eur J Pharmacol. Dec. 21, 2001;433(2-3):177-85.
Silashikanth et al., "A comparative study of raw garlic extract and tetracycline on caecal microflora and serum proteins of albino rats", Folia Microbiol (Praha). 1984;29(4):348-52.
Kim et al., "Differential regulation of NO availability from macrophages and endothelial cells by the garlic component S-allyl cysteine", Free Radic Biol Med. Apr. 1, 2001;30(7):747-56.
Colowick et al., "Glutathione—A Symposium" (pp. 21-30), 1054 Academic Press, New York.
Frerking et al., "Pulmonary surfactant: functions, abnormalities and therapeutic options", Intensive Care Med. Nov. 2001;27(11):1699-717.
Sharma et al., "Antibacterial property of Allium sativum Linn.: in vivo & in vitro studies", Indian J Exp Biol. Jun. 1977;15(6):466-8.
Augusti et al., "Therapeutic values of onion (Allium cepa L.) and garlic (Allium sativum L.)", Indian J Exp Biol. Jul. 1996;34(7):634-40.
Laude et al. (editors), "Coronaviruses—Molecular Biology and Virus-Host Interactions" (pp. 227-232), 1993 Kluwer Academic/Plenum Publishers, New York.
Laude et al. (editors), "Coronaviruses—Molecular Biology and Virus-Host Interactions" (pp. 235-244), 1993 Kluwer Academic/Plenum Publishers, New York.
Enjuanes et al. (editors), "Cronaviruses and Arteriviruses" (pp. 141-147), 1998 Plenum Press, New York.
Enjuanes et al. (editors), "Cronaviruses and Arteriviruses" (pp. 173-183), 1998 Plenum Press, New York.
Enjuanes et al. (editors), "Cronaviruses and Arteriviruses" (pp. 593-599), 1998 Plenum Press, New York.
Lavi et al. (editors), "The Nidoviruses (Coronaviruses and Arteriviruses)" (pp. 205-211), 2001 Kluwer Academic/ Plenum Publishers, New York.
Koch et al., "Garlic—The Science and Threapeutic Application of Allium sativum L. and Related Species" (pp. 148-174), 1996 Wilkins & Wilkins, Baltimore, MD.
Pasquier et al. (editors), "Oxidative Stress, Cell Activation and Viral Infection" (pp. 101-111), 1994 Birkhauser Verlag, Boston.
Pasquier et al. (editors), "Oxidative Stress, Cell Activation and Viral Infection" (pp. 143-153), 1994 Birkhauser Verlag, Boston.
Delany et al., "The Delany Sisters' Book of Everyday Wisdom" (p. 107), 1994 Kodansha International, New York.
Park et al. (editors), "Healthy Aging for Functional Longevity: Molecular and Cellular Interactions in Senescence" (pp. 327-335), 2001 Annals of the New York Academy of Sciences, vol. 928, New York.
Park et al. (editors), "Healthy Aging for Functional Longevity: Molecular and Cellular Interactions in Senescence" (p. 350), 2001 Annals of the New York Academy of Sciences, vol. 928, New York.
Park et al. (editors), "Healthy Aging for Functional Longevity: Molecular and Cellular Interactions in Senescence" (p. 353), 2001 Annals of the New York Academy of Sciences, vol. 928, New York.
Fuchin et al., "Ginger, Garlic & Green Onion as Medicine" (pp. 15-21), 1998 Pelanduk Publications, Malaysia.
Cavallito et al., "Allicin, the antibacterial principle of Allium sativum. I. Isolation. physical properties and antibacterial action", 1944 Journal of the American Chemical Society 66:1950-1951.
Cao et al., "Antioxidant capacity of tea and common vegetables", J Agric Food Chem. 1996 44:3426-31.
Lawson et al., "Low allicin release from garlic supplements: a major problem due to the sensitivities of alliinase activity", J Agric Food Chem. May 2001;49(5):2592-9.
Kaye et al. "Analysis of responses of garlic derivatives in the pulmonary vascular bed of the rat", J Appl Physiol. Jul. 2000;89(1):353-8.
Test et al., "Quantitative and temporal characterization of the extracellular H2O2 pool generated by human neutrophils", J Biol Chem. Jan. 10, 1984;259(1):399-405.
Wierzbicka et al., "Glutathione in food", Journal of Food Composition and Analysis 1989 2:327-37.
Kyung et al., "Antimicrobial activity of sulfur compounds derived from cabbage", J Food Prot. Jan. 1997;60(1):67-71.
Mirazimi et al., "Free thiol groups are essential for infectivity of human cytomegalovirus", J Gen Virol. Nov. 1999;80( Pt 11):2861-5.
Blackwell et al., "In vivo antioxidant treatment suppresses nuclear factor-kappa B activation and neutrophilic lung inflammation", J Immunol. Aug. 15, 1996;157(4):1630-7.
Ning et al., "Ribavirin inhibits viral-induced macrophage production of TNF, IL-1, the procoagulant fgl2 prothrombinase and preserves Th1 cytokine production but inhibits Th2 cytokine response", J Immunol. Apr. 1, 1998;160(7):3487-93.
Villa et al., "Glutathione protects mice from lethal sepsis by limiting inflammation and potentiating host defense", J Infect Dis. Apr. 15, 2002;185(8):1115-20.
Lau, "Suppression of LDL oxidation by garlic", J Nutr. Mar. 2001;131(3s):985S-8S.
Yang et al., "Mechanisms of inhibition of chemical toxicity and carcinogenesis by diallyl sulfide (DAS) and related compounds from garlic", J Nutr. Mar. 2001;131(3s):1041S-5S.
Lamm et al., "Enhanced immunocompetence by garlic: role in bladder cancer and other malignancies", J Nutr. Mar. 2001;131(3s):1067S-70S.
Hoshino et al., "Effects of garlic preparations on the gastrointestinal mucosa", J Nutr. Mar. 2001;131(3s):1109S-13S.
Blair et al., "Oral L-2-oxo-4-thiazolidine reduces bacterial translocation after radiation in the Fischer rat", J Surg Res. Oct. 1996;65(2):165-8.
Hon et al., "Clinical presentations and outcome of severe acute respiratory syndrome in children", Lancet. May 17, 2003;361(9370):1701-3.
Peiris et al., "Clinical progression and viral load in a community outbreak of coronavirus-associated SARS pneumonia: a prospective study", Lancet. May 24, 2003;361(9371):1767-72.
Donnelly et al., "Epidemiological determinants of spread of causal agent of severe acute respiratory syndrome in Hong Kong", Lancet. May 24, 2003;361(9371):1761-6.
Prasad et al., "Antioxidant activity of allicin, an active principle in garlic", Mol Cell Biochem. Jul. 19, 1995;148(2):183-9.

Ankri et al., "Antimicrobial properties of allicin from garlic", Microbes Infect. Feb. 1999;1(2):125-9.

Hamm et al., "Changes in the sulphydryl and disulphide groups in beef muscle proteins during heating", Nature. Sep. 18, 1965;207(5003):1269-71.

Bernard et al., "Efficacy and safety of recombinant human activated protein C for severe sepsis", N. Engl J Med. Mar. 8, 2001;344(10):699-709.

Chance et al., "Hydroperoxide metabolism in mammalian organs", Physiol Rev. Jul. 1979;59(3):527-605.

Tsai et al., "Antiviral Properties of Garlic: in vitro Effects on Influenza B, Herpes Simplex and Coxsackie Viruses", Planta Med. Oct. 1985;51(5):460-1.

Wagner et al., "Effects of garlic constituents on arachidonate metabolism", Planta Med. Jun. 1987;53(3):305-6.

Weber et al., "In vitro virucidal effects of Allium sativum (garlic) extract and compounds", Planta Med. Oct. 1987;58(5):417-23.

Lawson et al., "Pre=hepatic fate of the organosulfur compounds derived from garlic (Allium sativum)" Planta Med. 1993 59:A688.

Imai et al., "Antioxidant and radical scavenging effects of aged garlic extract and its constituents", Planta Med. Oct. 1994;60(5):417-20.

Lawson et al., "Allicin release under simulated gastrointestinal conditions from garlic powder tablets employed in clinical trials on serum cholesterol", Planta Med. Feb. 2001;67(1):13-8.

Andrianova et al., "[Effect of long-acting garlic tablets "allicor" on the incidence of acute respiratory viral infections in children]", Ter Arkh. 2003;75(3):53-6; Abstract from PubMed PMID: 12718222.

Meyer et al., "Inflammation and surfactant", Paediatr Respir Rev. Dec. 2002;3(4):308-14.

Billing et al., "Antimicrobial functions of spices: why some like it hot", Q Rev Biol. Mar. 1998;73(1):3-49.

Bauer et al., "Comparison of systemic cytokine levels in patients with acute respiratory distress syndrome, severe pneumonia, and controls", Thorax. Jan. 2000;55(1):46-52.

White et al., "Toxicity evaluations of L-cysteine and Procysteine, a cysteine prodrug, given once intravenously to neonatal rats", Toxicol Lett. Jul. 1993;69(1):15-24.

Torchinskii, "Sulfhydryl and Disulfide Groups of Proteins" (pp. 94-5), Translated from Russian, 1974 Consultants Bureau, New York.

Burdock, "Fenaroli's Handbook of Flavor Ingredients" (p. 53), Fourth edition, 2001 CRC Press, Boca Raton, Florida.

Groeneveld et al., "Vascular pharmacology of acute lung injury and acute respiratory distress syndrome", Vascul Pharmacol. Nov. 2002;39(4-5):247-56.

* cited by examiner

ORGANOSULFUR PRODRUGS FOR THE PREVENTION AND TREATMENT OF INFECTIOUS DISEASES

This application claims the benefit of provisional application No. 60/472,791, filed May 23, 2003.

1. BACKGROUND OF THE INVENTION

1.1 Field of the Invention

The present invention applies generally to the prevention and treatment of infectious diseases and/or pathogenic immune system response, and is more specifically illustrated in the prevention and treatment of bacterial infections, pneumonia, and Acute Respiratory Distress Syndrome (ARDS).

2. DEFINITIONS, ORGANOSULFUR GLOSSRY, AND ABBREVIATIONS

2.1 Definitions and Organosulfur Glossary

Allicin: Chemical name DiAllylThioSulfinate; chemical formula:

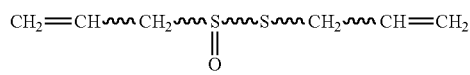

A compound formed by crushing garlic (which allows the enzymatic conversion by alliinase of alliin to allicin) that produces many of the medicinal benefits that are attributed to garlic.

Allium related compounds: Organosulfur compounds that are either derived from alliums (e.g. garlic or onion) through chemical or metabolic means, or are related to such compounds in specific ways such that they can reasonably be expected to exhibit similar medicinal properties.

Allyl mercaptan: AllylSH, chemical name AllylThiol; chemical formula:

$CH_2=CH\sim CH_2\sim SH$

The primary pre-hepatic metabolite of allicin. In the presence of glutathione, two allyl mercaptan molecules are produced from each allicin molecule. This reaction is known to occur very rapidly within red blood cells.

Allyl mercapto radical: AllylS*, allyl mercaptan without the terminal hydrogen atom of the SH group, resulting in an unpaired electron on the sulfur atom which is available for bonding to the remainder of a larger molecule.

$CH_2=CH\sim CH_2\sim S*$

Cysteine: CySH, A sulfur-containing amino acid with the formula:

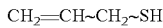

Cysteine is not to be confused with cysteine disulfide (CyS~SCy, generally referred to as cystine).

Cysteinal radical: CyS*, cysteine without the terminal hydrogen atom of the SH group, resulting in an unpaired electron on the sulfur atom. A cysteinal radical will typically be covalently bonded to another atom that is part of the complete molecule (e.g. with the sulfur atom of an allyl mercapto radical to form an S-AllylMercaptoCysteine molecule).

DiAllylDisulfide: DADS, (also abbreviated as AllylS~SAllyl), the disulfide formed from two AllylMercapto radicals bonded together. Equivalent to deoxygenated allicin.

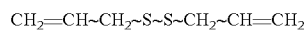

Glutathione: GSH, the most omnipresent biothiol, a tripeptide composed of the amino acids glutamyl, cysteine, and glycine. The symbol GSH uses "G" to represent the bulk of the molecule and "SH" to represent the thiol portion of the molecule, leading to symbols such as GS– for the ionized form of glutathione, GS* for the free radical form, and GSSG for the "oxidized" disulfide form.

Oxidized: The reaction product that tends to be produced when the reactants are exposed to oxygen, such as the conversion of thiols to disulfides. For example, if two cysteine molecules are exposed to reactive oxygen, their terminal "SH" hydrogen atoms tend to eventually disassociate from the molecules (e.g. they form thiyl radicals) and join together to form cysteine disulfide (also known as cystine). The two "abstracted" hydrogen atoms have combined with the reactive oxygen to form an H2O molecule.

Oxidation tends to remove electrons from molecules. The removal of a hydrogen atom from a molecule is also considered to be oxidation, because this also involves the removal of an electron. Conversely, the removal of a proton (H+) is not considered oxidation, because the electron is left on the molecule.

Oxygenated: Another form of oxidation product, where an oxygen atom has been added to a molecule.

Reactive Oxygen Species: ROS, oxygen-containing molecules that are capable of producing oxidative damage to other molecules. Many, but not all, ROS are free radicals. Examples include (ISBN0306457563):

$H_2O_2$ (hydrogen peroxide), $*O_2-$ (superoxide radical), $*OH$ (hydroxyl radical)

HOCl (hypoclorus acid), ONOO— (peroxynitrite), $O_2^1$ (singlet oxygen), $O_3$ (ozone)

*NO (nitric oxide), and $*NO_2$ (nitrogen dioxide).

Reduced: The converse of oxidized. For example, when the terminal sulfur of a cystienal radical is bonded to a hydrogen atom to form a cysteine molecule, the cysteine is in its reduced state.

SAMC: S-AllylMercaptoCysteine, the molecule formed by a Cysteinal radical disulfide bonded to an AllylMercapto radical.

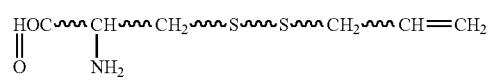

SAMG: S-AllylMercaptoGlutathione (also abbreviated as AllylS~SG), the molecule formed by a glutathione radical disulfide bonded to an AllylMercapto radical.

Thiol: Any molecule that includes one or more terminal sulfhydrate (SH) groups.

Thiyl radical: Multiple covalently bonded atoms that are considered to be a group terminating with a sulfur atom that has an unpaired electron, Normally, a thiyl radical will be covalently bonded to another atom that is part of the complete molecule, although it could alternatively be an unbonded "free radical." For example, two cysteinal radicals with a covalent bond between their sulfur atoms (a disulfide bond) form a cysteine disulfide molecule (CyS~SCy, cystine).

2.2 Other Abbreviations

ARDS: Acute Respiratory Distress Syndrome

SARS: Severe Acute Respiratory Syndrome

3. References

For articles contained in books, the first reference is the book and the following reference(s) are the article(s).

A139:333; V. Dirsch et al; Effect of Allicin and Ajoene, two Compounds of Garlic, on Inducible Nitric Oxide Synthase; Atherosclerosis 139:333.

AA25:182; P. Mayeux et al; The Pharmacological effects of allicin, a constituent of garlic oil; Agents and Actions 25:182.

AAC22:108; C. Powers, D. Peavy, and V. Knight; Selective Inhibition of Functional Lymphocyte Subpopulations by Ribavirin; Antimicrobial Agents and Chemotherapy 22, page 108.

ABC52:2383; M. Tada et al; Nematicidal and Antimicrobial Constituents from Allium grayi Regel and Allium fistulosum L. var. caespiitosum; Agricultural and Biological Chemistry 52:2383.

AIT18:189; P. Josling; Preventing the Common Cold With a Garlic Supplement: A Double-Blind, Placebo-Controlled Study; Advances In Therapy 18:189.

AJCN74:756; M. Buono et at; Total Sulfur Amino Acid Requirement in Young Men as Determined by Indicator Amino Acid Oxidation; American Journal of Clinical Nutrition 74:756.

AJM91:3C-140S; W. Droge et al. Modulation of Lymphocyte Functions and Immune Response by Cysteine and Cysteine Derivatives; The American Journal of Medicine 91:3C-140S.

AJMS307:119; P. Morris and G. Bernard; Significance of Glutathione in Lung Disease and Implications for Therapy; The American Journal of the Medical Sciences 307:119.

AJP275:L283; M. Fallon et al; Garlic Prevents Hypoxic Pulmonary Hypertension in Rats; American Journal of Physiology 275:L283.

AJPLCMP265:L501; J. A. Leff et al; Postinsult treatment with N-acetyl-L-cysteine decreases IL-1-induced neutrophil influx and lung leak in rats; American Journal of Physiology Lung, Cell, and Molecular Physiology 265:L501.

AJPLCMP278:L1240; P. Knight et al; Acid Aspiration Increases Sensitivity to Increased Ambient Oxygen Concentrations; American Journal of Physiological Cell and Molecular Physiology 278, page L1240.

AM17:903; M. G. Johnson and R. H. Vaughn; Death of Salmonella typhimurium and Escherichia coli in the Presence of Freshly Reconstituted Dehydrated Garlic: and Onion; Applied Microbiology 17:903.

ARB52:711; A. M. Meister, M. E. Anderson; Glutathione; Annual Review of Biochemistry 52:711.

ARZN28:250; J. Iravani et al; N-Acetylcysteine and Microciliary Activity in Mammalian Airways; Arzneimittel-Forschung 28:250.

BBA1379:233; A. Rabinkov, T. Miron, L. Konstantinovski, M. Wilchek, D. Mirelman, L. Weiner, 1998; The mode of action of allicin: trapping of radicals and interaction with thiol containing proteins; Biochimica et Biophysica Acta 1379:233.

BBA1463:20; T. Miron, A. Rabinkov, D. Mirelman, M. Wilchek, L. Weiner, 2000; The mode of action of allicin: its ready permeability through phospholipid membranes may contribute to its biological activity. Biochimica et Biophysica Acta 1463:20.

BJ63:514; E. Wills; Enzyme Inhibition by Allicin, the Active Principle of Garlic; The Biochemical Journal 63:514.

BMCCD2:2; M. Hayden and S. Tyagi; Is Type 2 Diabetes Mellitus a Vascular Disease (Atheroscleropathy) with hyperglycemia a late manifestation? The role of NOS, NO, and Redox Stress; BioMed Central Cardiovascular Diabetology 2:2.

BST23:S136; I. Das et al; Nitric Oxide Synthase is a Unique Mechanism of Garlic Action; Biochemical Society Transactions 23:S136.

C108:1315; G. U. Meduri et al; Plasma and BAL Cytokine Response to Corticosteroid Rescue Treatment in Late ARDS; Chest 108:1315.

C111:1157; Why Does Lactic Acidosis Occur in Acute Lung Injury?; Chest 111:1157.

C111:1301; J. Kellum et al; Release of Lactate by the Lung in Acute Lung Injury; Chest 111:1301.

C111:1306; A. S. Headley, E. Tolley, and G. U. Meduri; Infections and the Inflammatory Response in Acute Respiratory Distress Syndrome; Chest 111:1306.

C112:164; G. Bernard, et al; A Trial of Antioxidants N-acetylcysteine and Procysteine in ARDS; Chest 112:164

CIRCUL84:516; S. Kokura et al; Molecular Mechanisms of Neutrophil-Endothelial Cell Adhesion Induced by Redox Imbalance; Circulation Research 84:516.

COCC7:1; W. Lee and G. Downey; Neutrophil activation and Acute Lung Injury; Current Opinion in Critical Care 7:1.

CR61:725; H. Shirin et al; Antiproliferative Effects of S-Allylmercaptocysteine on Colon Cancer Cells When Tested Alone or in Combination with Sulindac Sulfide; Cancer Research 61:725.

DMD27:835; C. Teyssier et al; Metabolism of Dially Disulfide by Human Liver Microsomal Cytochromes P-450 and Flavin-Containing Monoxoogenases; Drug Metabolism and Disposition 27:835.

EJP433:177; I. Sumioka, et al; Therapeutic effect of S-allylmercaptocysteine on acetaminophen-induced liver injry in mice; European Journal of Pharmacology 433:177.

FM29:348; K. N. Silashikanth, et al; A Comparative Study of Raw Garlic Extract and Tetracycline on Caecal Microflora and Serum Proteins of Albino Rats; Folia Microbiologica 29:348.

FRBM30:747; K. Kim et al; Differential Regulation of NO Availability from Macrophages and Endotheial Cells by the Garlic Component S-Allyl Cysteine; Free Radical Biology & Medicine 30:747.

GAS1953; S. Colowick et al; Glutathione—A Symposium; Academic Press, New York, 1954.

ICM27:1699; I. Frerking et al; Pulmonary surfactant: functions, abnormalities and therapeutic options; Intensive Care Medicine 27:1699.

IJEB15:466; V. Sharma et al; Antibacterial Property of Allium SativumLinn.: in vivo & in vitro Studies; Indian Journal of Experimental Biology 15:466.

IJEB34:634; K. T. Agusti; Therapeutic values of onion (Allium cepa L.) and garlic (Allium sativum L.); Indian Journal of Experimental Biology 34:634.

ISBN0306445999; Edited by H. Laude and J. Vautherot, 1993; Coronaviruses—Molecular Biology and Virus-Host Interactions; Kluwer Academic/Plenum Publishers, New York.

ISBN0306445999:227; E. Snijder, A. Wassenaar, and W. Spaan; Proteolytic Processing of the N-Terminal Region of the Equine Arteritis Virus Replicase (in ISBN0306445999).

ISBN0306445999:235; E. Snijder et al; The Coronavirus Superfamily (in ISBN0306445999).

ISBN0306459108; Edited by L. Enjuanes et al., 1998; Coronaviruses and Arteriviruses; Plenum Press, New York.

ISBN0306459108:141; J. Herold et al; Characterization of a Papain-Like Cysteine-Proteinase Encoded by the Gene 1 of the Human Coronavirus HCV 229E (in ISBN0306459108).

ISBN0306459108:173; K. Lim and D. Liu; Characteristics of a Papain-Like Proteinase Domain Encoded by ORF1a of the Coronavirus IBV and Determination of the C-Terminal Clevage Site of an 87 kDa Protein (in ISBN0306459108)

ISBN0306459108:593; J. Beyer et al; Experimental Studies on the Pathogenesis of Respiratory Disease (in ISBN0306459108).

ISBN0306466341; Edited by E. Lavi, S. Weiss, and S. Hingley, 2001; The Nidoviruses (Coronaviruses and Arteriviruses); Kluwer Academic/Plenum Publishers, New York.

ISBN0306466341:205; K. Chang and J. Gombold; Effects of Amino Acid Insertions in the Cysteine-rich Domain of the MHV-A59 Spike Protein on Cell Fusion (in ISBN0306466341).

ISBN0683181475H. P. Koch and L. D. Lawson, 1996; GARLIC The Science and Therapeutic Application of Allium sativum L. and Relates Species; Williams & Wilkins, Baltimore MD.

ISBN0683181475:148; H. P. Koch and L. D. Lawson; Effects on Blood Pressure, Vascular Resistance, and Heart Function (in ISBN0683181475).

ISBN08176229416; Edited by C. Pasquier, R. Oliver, C. Auclair, and L. Packer, 1994; Oxidative Stress, Cell Activation and Viral Infection; Birkhauser Verlag, Boston, Mass.

ISBN08176229416:101; A. Meister; The Antioxidant Effects of Glutathione and Ascorbic Acid (in ISBN08176229416).

ISBN08176229416:143; G. Rotilio, L. Knoepfel, C. Steinkuhler, A. Palamara, M. Ciriolo, and E. Garaci; Effects of Intracellular Redox Stress on Cellular Regulation and Viral Infection (in ISBN08176229416).

ISBN1568360428; S. and E. Delany with A. Hearth, 1994; The Delany Sisters' Book of Everyday Wisdom; Kodansha International, New York.

ISBN1568360428:107; The Order of the Day (in ISBN1568360428).

ISBN1573312851; Edited by S. Park et al; Healthy Aging for Functional Longevity: Molecular and Cellular Interactions in Senescence; Annals of the New York Academy of Sciences, Volume 928.

ISBN1573312851:327; H. Chung et al; The Inflammation Hypothesis of Aging: Molecular Modulation by Caloric Restriction; (in ISBN1573312851).

ISBN1573312851:350; J. Kim et al; Analysis of Redox Status in Serum During Aging (in ISBN1573312851).

ISBN1573312851:353; H. Kim et al; Contribution of Cyclooxygenase to Age-related Oxidative Stress (in ISBN1573312851).

ISBN9679786846; W. Fuchin and D. Yuhua 1998; Ginger, Garlic & Green Onion as Medicine; Pelanduk Publications, Malaysia.

JAFC44:3413; K. M. Wall et al; Protein in Varietally Derived Apple Juices; Journal of Agricultural and Food Chemistry 44:3413.

JAFC44:3426; G. Cao et al; Antioxidant Capacity of Tea and Common Vegetables; Journal of Agricultural and Food Chemistry 49:3126 44:3426.

JAFC49:2592; L. Lawson and Z. Wang, 2001; Low Allicin Release from Garlic Supplements: a Major Problem Due to the Sensitivities of Alliinase Activity; Journal of Agricultural and Food Chemistry 49:2592.

JAP89:353; A. Kaye et al; Analysis of Responses of Garlic Derivatives in the Pulmonary Vascular Bed of the Rat; Journal of Applied Physiology 89:353.

JBC259:399; S. T. Test et al; Quantitative and Temporal Characterization of the Extracellular H2O2 Pool Generated by Human Neutrophils; The Journal of Biological Chemistry 259:399.

JFCA2:327; G. Wierzbicka et al; Glutathione in Food; Journal of Food Composition and Analysis 2:327.

JGVI80:2861; A. Mirazimi et al; Free thiol groups are essential for infectivity of human cytomegalovirus; Journal of General Virology 80:2861.

JI157:1630; T. S. Blackwell et al; In Vivo Antioxidant Treatment Suppresses Nuclear Factor-kB Activation and Neutrophilic Lung Inflammation; The Journal of Immunology 157:1630.

JI160:3487; Q. Ning et al; Ribavirin Inhibits Viral-Induced Macrophage Production of TNF, IL-1, the Procoagulant fg12 Prothrombinase and Preserves Th1 Cytokine Production But Inhibits Th2 Cytokine Response; Journal of Immunology 160:3487.

JID185:1115; P. Villa et al; Glutathione Protects Mice from Lethal Sepsis by Limiting Inflammation and Potentiating Host Defense; The Journal of Infectious Diseases 185:1115.

JN131:985S; B. Lau; Suppression of LDL Oxidation by Garlic; The Journal of Nutrition 131:985S, supplement 3S.

JN131:1010S; C. Borek; Antioxidant Health Effects of Aged Garlic Extract; The Journal of Nutrition 131:1010S, supplement 3S.

JN131:1041S; C. Yang et al; Mechanisms of Inhibition of Chemical Toxicity and Carcinogenesis by Diallyl Sulfide (DAS) and Related Compounds from Garlic; The Journal of Nutrition 131:1041S, supplement 3S.

JN131:1067S; D. Lamm and D. Riggs; Enhanced Immunocompetence by Garlic: Role in Bladder Cancer and Other Malignancies; The Journal of Nutrition 131:1067S, supplement 3S.

JN131:1109S; T. Hoshino et al; Effects of Garlic Preparations on the Gastrointestinal Mucosa; The Journal of Nutrition 131:1109S, supplement 3S.

JSR65:165; S. L. Blair et al; Oral L-2-Oxo-4-thiazolidine Reduces Bacterila Translocation after Radiation in the Fischer Rat; Journal of Surgical Research 65:165.

L03:4127; K. Hon et al; Clinical presentations and Outcome of Severe Acute Respiratory Syndrome in Children; The Lancet 361:1701.

L03:4432; J. Peiris et al; Clinical Progression and Viral Load in a Community Outbreak of Coronavirus-associated SARS pneumonia: A Prospective Study; The Lancet 361:1767.

L03:4453; C. Donnelly et al; Epidemiological Determinants of Spread of Causal Agent of Severe Acute Respiratory Syndrome in Hong Kong; The Lancet 361:1761.

MBC148:183; K. Prasad et al; Antioxidant Activity of Allicin, an active Principle in Garlic; Molecular and Cellular Biochemistry 148:183.

MI2:125; S. Ankri, D. Mirelman; Antimicrobial Properties of Allicin from Garlic; Microbes and Infection 2:125. N207:1269; R. Hamm and K Hoffman; Changes in the Sulphydryl and Disulfide Groups in Beef Muscle Proteins During Heating; Nature 207:1269.

NEJM344:699; G. Bernard et al; Efficacy and Safety of Recombinant Human Activated Protein C for Severe Sepsis; The New England Journal of Medicine 344:699.

PHRE59:527; B. Chance et al; Hydroperoxide Metabolism in Mammalian Organs; Physiological Reviews 59:527.

PM51:460; Y. Tsai et al; Antiviral Properties of Garlic: In vitro Effects on Influenza B, Herpes Simplex, and Coxsackie Viruses; Planta Medica 51:460.

PM53:305; H. Wagner et al; Effects of Garlic Constituents on Arachidonate Metabolism; Planta Medica 53:305.

PM58:417; N. Weber et al; In Vitro Virucidal Effects of Allium sativum (Garlic) Extracts and Compounds; Planta Medica 58:417.

PM59:A688; L. Lawson and Z. Wang, 1993; Pre-Hepatic Fate of the Organosulfur Compounds Derived from Garlic (Allium sativum); Planta Medica 59:A688.

PM60:417; J. Imai et al; Antioxidant and Radical Scavenging Effects of Aged Garlic Extract and its Constituents; Planta Medica 60:417.

PM67:13; L. Lawson, et al; Allicin Release under Simulated Gastrointestinal Conditions from Garlic Powder Tablets Employed in Clinical Trials on Serum Cholesterol; Planta Medica 67:13.

PMID12718222; I. V. Andrianova, et al; [Effect of long-acting garlic tablets "allicor" on the incidence of acute respiratory viral infections in children]; Ter Arkh. 20003;75(3):53 [Article in Russian, PubMed abstract 12718222].

PRR3:208; K. C. Meyer and J. J. Zimmerman; Inflammation and Surfactant; Paediatric Respiratory Reviews 3:308.

QRB73:3; J. Billing and P. W. Sherman; Antimicrobial Functions of Spices: Why Some Like it Hot; The Quarterly Review of Biology 73:3.

T55:46; T. Bauer et al; Comparison of systemic cytokine levels in patients with acute respiratory distress syndrome, severe pneumonia, and controls; Thorax 55:46.

TL69:15; R. White et al; Toxicity Evaluations of L-cysteine and Procysteine, a Cysteine Prodrug, Given Once Intravenously to Neonatal Rats; Toxicology Letters 69:15.

Torchinskii:1974; Y. Torchinskii, 1974; Sulfhydryl and Disulfide Groups of Proteins; Translated from Russion by H. Dixon, Consultants Bureau, New York.

US005451412A; G. Bounous et al; Biologically Active Undenatured Whey Protein Concentrate as Food Supplement; U.S. Pat. No. 5,451,412.

VASP39:247; A. B. Johan Groeneveld; Vascular pharmacology of acute lung injury and acute respiratory distress syndrome; Vascular Pharmacology 39:247.

WO:01/36450; T. Miron et al; S-Allylmercaptoglutathione and Uses Thereof; World Intellectual Property Organization WO 01/36450 A1.

4. DESCRIPTION OF THE PRIOR ART 4.1 Relationship with the Organosulfur Compounds from Alliums Although the organosulfur compounds utilized by the present invention (e.g. protein-bound SAMC) are not necessarily constituents of alliums, they share a variety of properties with alliums. Hence known properties of alliums are germane to an appreciation of the invention and are reviewed here briefly.

4.1.1 Alliums and their Medicinal Benefits

Garlic, onions, and other alliums have been reputed to have beneficial medicinal properties for thousands of years. Traditional medicine has yielded a vast number of compositions containing garlic and/or onions for the treatment of a wide variety of conditions (ISBN9679786846, EPMR6:56, EPMR6:115).

Medicinal uses include the prevention and treatment of diseases related to the heart and circulatory system, microbial infections, cancer, respiratory diseases, hypoglycemia, and as an antidote for heavy metal poisoning and other toxins (ISBN0683181475, pages 135-211).

In the prevention of bacterial infections, garlic is exceptional as an antibiotic because it produces a pro-biotic response, encouraging the maintenance of a healthy intestinal flora (FM29:348). It simultaneously inhibits the "bad" bacteria (streptococci, coliforms, e. coli, salmonellae) by a large factor (100×) while inhibiting the "good" lactobacteria by a much smaller factor (10×). Another interesting aspect of garlic is the apparent inability of most bacteria to develop resistance to it (MI2:125), although apparently the lactic bacteria have evolved some tolerance.

In addition to disease prevention, garlic and other alliums have been used to provide general health benefits such as antioxidant protection, strengthened immune system, anti-hepitoxic protection, anti-inflammatory protection, improved digestion, and even for repelling insects (ISBN0683181475, pages 135-211).

Daily garlic consumption has been associated with health maintenance and is recommended for successful aging (ISBN1568360428:107). Literally thousands of scientific papers have been published on garlic, allicin, and related compounds, with 2240 references listed in ISBN0683181475, pages 235-319.

4.2 Allicin—an Effective Ingredient from Alliums, Especially Garlic.

The first medicinal property of garlic to be studied with modern scientific methods was its antibacterial action (JACS66:1950). The active ingredient was isolated and given the name allicin.

The chemical structure of allicin was determined to be:

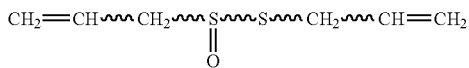

Numerous allium-related organosulfur compounds other than allicin have been found to provide medicinal benefits; however the benefits attributed to allicin tend to be the superset, in part because many of these other compounds produce similar metabolites in vivo (PM59:A688).

In the presence of glutathione and an active glutathione-reductase system, allicin is rapidly metabolized to allyl-mercaptan. This can be shown to occur in less than one minute by the analysis of blood cells that have been exposed to allicin (PM59:A688). The extremely high permeability of biological membranes to allicin also contributes to its biological activity (BBA1463:20).

Other garlic related organosulfur compounds that metabolize in blood to allyl mercaptan include diallyl trisulfide, diallyl disulfide, ajoene, and SAMC (PM59:A688). It has been proposed that "in vitro or ex vivo studies of the mechanism of action of these compounds should not use the parent compounds, but rather should use allyl mercaptan, or possibly a further metabolite of allyl mercaptan" (ISBN0683181475, page 214).

4.2.1 Allicin is a Broad Spectrum Anti-Microbial Agent that is Effective in Preventing Infections, Including the Common Cold Allicin has been shown to be a broad spectrum antimicrobial agent that significantly inhibits many strains of bacteria, fungi, viruses, and parasites (MI2:125). It has even been shown to be effective in the prevention and treatment of the common cold (AIT18:189), reducing the frequency of infection (24 vs 65 for the placebo group), and reducing the duration of symptoms to an average of 1.5 days (vs 5 days for the placebo group).

The mechanism of action was initially proposed to be due to allicin's reaction with cysteine (JACS66:1952), eliminating free SH groups (via disulfide formation) essential to bacterial proliferation. Allicin was subsequently shown to be a very potent inhibitor of "SH-enzymes" (BJ63:514). This model for its mechanism of action is still commonly accepted (MI2:125) and is supported by experimental evidence (BBA1379:233).

4.2.2 Allicin can be a Powerful Antioxidant

Allicin is generally an antioxidant, but also has some oxidant properties. It has been shown to scavenge H2O2 and *OH radicals in a concentration-dependent manner (MCB148:183). Although not observed by the authors of MCB148:183, their FIG. 7 shows that although at low to medium-high concentrations allicin is an antioxidant, at high concentrations it behaves as an oxidant resulting in the actual formation of *OH radicals.

In a study of the suppression of LDL oxidation by garlic related compounds (JN131:985S), S-allylcysteine, N-acetyl-S-allylcysteine, allin, and especially SAMC were shown to significantly reduce Cu2+ induced LDL oxidation, but allicin increased the LDL oxidation to almost 3× the level of the control.

In a study of the total antioxidant capacity of 22 vegetables measuring the reduction of peroxyl radicals (*OOH), hydroxyl radicals (*OH), and of Cu2+ catalyzed free-radical chain reactions, garlic homogenate rated a "total antioxidant score" of 23.2 (second only to kale), approximately 3 times the average (JAFC44:3426). Interestingly, the garlic homogenate showed significant antioxidant capacity against Cu2+ induced oxidation (contrary to the effect of allicin reported in JN131:985S).

In a chemiluminescense assay of the antioxidant properties of eight commercial garlic products, only the "AGE" product (Aged Garlic Extract, from Wakugana Corporation, www.kyolic.com) had a net antioxidant activity (JN131:1010S). The other products all contained garlic powder and produced allicin upon ingestion. The "AGE" product contains primarily the water-soluble compounds S-allylcysteine (SAC) and SAMC, but also contains the lipid-soluble compounds diallyl sulfide, triallyl sulfide, and DADS.

In another study comparing the constituents of AGE with garlic extract, a chemiluminescense assay shows raw or heated garlic extract to be pro-oxidant, but AGE is antioxidant (PM60:417). Of the water-soluble components of AGE, SAMC was shown to be by far the most effective antioxidant (by approximately a factor of two compared to the other compounds).

But Aged Garlic Extract also contains protein F4 from garlic, which is an immunostimulant that can cause inflammation (JN131:1067S). In this case, the oxidants are produced in vivo by the immune system itself.

4.2.3 Toxicity of Allicin and Raw Garlic Powder

The comparative toxicity of different garlic preparations containing different garlic constituents has been studied (JNI31:1109S). Endoscopic examination of the stomach mucosa of dogs 24 hours after the direct administration of raw garlic powder detected erosion at 15 out of 18 sites. But if the garlic powder had been boiled (to inactivate the allinase, thereby eliminating any allicin), no erosion was observed, but some redness appeared. When the "AGE" garlic product was administered (which contains no allicin), no erosion or redness was observed.

Enteric-coated garlic products release their contents (including enzymatically produced allicin) into the intestine (instead of the stomach). But examination of the intestine of a dog 3 hours after the administration of three tablets showed damaged and lost epithelial cells at the top of crypts (JN131:1067S). The authors questioned the safety of enteric-coated garlic products and recommended the use of AGE instead.

4.2.4 Sources of Allicin
4.2.4.1 Raw Garlic

When garlic is crushed, the enzyme allinase converts the (previously separately compartmentalized) allin instantly to allicin (ISBN0683181475, page 48). Interestingly, for the garlic plant itself this produces the antimicrobial agent precisely when and where it is needed, in response to the lysing of its cell walls by bacteria or fungi. (For humans it burns the mouth, probably due to oxidation.)

4.2.4.2 Garlic Supplements That Produce Allicin from Allin

Dietary supplements traditionally do not directly incorporate allicin because of allicin's poor stability. Dietary supplements instead generally have contained the allicin precursor alliin along with the enzyme alliinase with an enteric coating utilized to prevent them from mixing together until they reach the intestine. The allicin release from these products has been problematic. If the coating dissolves too soon the stomach acids instantly deactivate the alliinase enzyme, but if the coating lasts too long the reaction never occurs. In a survey of dietary supplements published in 2001, only one supplement achieved its claimed bioavailable allicin yield (JAFC49:2592).

For example, in 1993 a change in the manufacturing process for "Kwai" garlic tablets caused their allicin yield to change from 73% of the theoretical yield to only 23%. This was discovered only after several clinical trials were conducted using these tablets (on the serum cholesterol lowering ability of garlic). In retrospect, the results of the various clinical trials can be seen to correlate with the actual allicin release from the various products tested (PM67:13).

The failure of garlic tablets to consistently meet their claimed allicin yield remains a problem even today (see www.consumerlab.com/results/garlic.asp).

4.2.4.3 Allicin Supplements Containing Pre-Formed Allicin

A process has been developed for stabilizing allicin, allowing the non-enzymatic delivery of allicin in a capsule. These are currently only available from Allicin International (www.allimax.com). The actual allicin content is not printed on the label, nor is this information available from the manufacturer. Instead, the allicin content of each Allimax capsule is described as the same amount of allicin as you get from 1 clove of top quality garlic.

4.2.4.4 In vivo Allicin Production from DADS

Allicin is produced in the liver from Diallyl disulfide (DADS) via several cytochrome P-450 enzymes (e.g. CYP2E1) and flavin-containing monooxygenases (DMD27:835). Thus the in vivo production of allicin can be accomplished by any mechanism that delivers DADS to the liver. (Note: the DADS molecule is identical to an allicin molecule with the oxygen atom removed. Conversely, the oxygenation of a sulfur atom in a DADS molecule results in the formation of an allicin molecule.)

The activity of the enzymes is moderate (up to 121 pmol/min/pmol CYP2D6), resulting in approximately 30% conversion of DADS to allicin in 30 minutes (DMD27:835).

The CYP2E1 enzyme can also oxygenate the allium-related compound diallyl sulfide to diallyl sulfoxide (DASO) and to diallyl sulfone (DASO2), which have been shown to inhibit carcinogenesis (JN131:1041S).

4.3 Cysteine—Amino Acid, Biothiol, and Glutathione Precursor

Cysteine is a sulfur containing amino acid which is an important constituent of proteins. The active site of many enzymes (e.g. proteases) involves cysteine, where the reactivity of the SH group contributes to the activity of the enzyme. Maintenance of the tertiary structure of proteins depends on the formation of disulfide bonds between pairs of cysteines within the protein. Disulfide bonds can also link adjacent proteins, providing structure to tissues.

Cysteine is a thiol (it has a terminal "SH" group) and shares many properties with other thiols. It is able to participate in thiol-disulfide exchange reactions with almost all other thiols and disulfides resulting in a wide variety of mixed disulfides. Thiol-disulfide exchange reactions allow the formation of disulfide bonds (which are covalent bonds and quite strong) and their later separation with no energy involved (other than the thermal energy that brings them together or apart).

Cysteine tends to auto-oxidize to cysteine disulfide (cystine) in the presence of oxygen. Inside cells the "reductive" environment provided by the maintenance of reduced glutathione (by glutathione reductase) tends to keep the cysteine reduced, but in an extracellular environment cysteine disulfide forms. Some types of cells can absorb cysteine disulfide, internally reduce it to cysteine, and then excrete the cysteine to the extracellular environment (AJM91_3C:140S). This appears to be necessary for proper lymphocyte function and immune response.

Cysteine exhibits toxicity in large dosage, but non-toxic prodrugs exist (TL69:15), such as N-acetylcystine (NAC) and L-2-Oxo-thiazolidine (OTZ) (JSR65:165). The low solubility of cystine can result in the formation of kidney stones.

4.4 Glutathione—The Mother of all Antioxidants

Glutathione (GSH) serves as a critical antioxidant and is perhaps the only molecular antioxidant whose total depletion can directly cause death. In part, this is due to the ability of most antioxidants to "spare" for each other (even GSH can be partially spared by ascorbic acid). But it is also due to the ability of the glutathione reductase system to recycle almost all other antioxidants to their reduced state (ISBN08176229416:101). Therefore, insufficient GSH can result in the accumulated oxidation of various other antioxidants.

Glutathione's antioxidant properties are partially due to the various GSH-peroxidase enzymes that use GSH to reduce peroxides (e.g. hydrogen peroxide, H2O2), producing GSSG in the process, which in turn is reduced back to 2 GSH by GSH-reductase (ARB52:711). But glutathione can also react non-enzymatically to reduce H2O2, scavenge *O2 (superoxide) radicals, and detoxify reactive nitrogen (e.g. nitric-oxide) compounds.

Glutathione is also necessary for the detoxification of a wide variety of toxic substances (ARB52:711). The various GSH-transferase enzymes bind the toxic substances to glutathione molecules, which are then excreted from the cell (and ultimately from the body). Glutathione is a coenzyme for other detoxification processes, including the methylation of arsenic. Insufficient GSH (e.g. from depletion due to alcohol consumption) is responsible for acetaminophen (Tylenol®) toxicity, which is reported to be the second largest cause of toxic drug ingestion in the United States (BMCCC6:155).

4.5 Glutathione and/or Cysteine Deficiency 4.5.1 Dietary Sources Glutathione, Cysteine and Methionine Cysteine deficiency may be common even in people who believe they eat enough protein. Many sources of dietary protein have low cysteine and methionine (another amino acid that can be converted to cysteine in vivo) content. People who do not eat much meat are especially at risk, especially the elderly. Even the official FAO/WHO/UNU recommendation for daily dietary cysteine+methionine consumption is reportedly low by almost a factor of two (13 mg/kg instead of 25 mg/kg) due to an arithmetic error when the requirements were determined experimentally in 1955 (AJCN74:756).

Glutathione in food varies dramatically such that well fed Americans are reported to exhibit a 40:1 range in its consumption (JFCA2:327). However, dietary glutathione probably has no special significance other than as a source of cysteine. The glutathione inside cells is created from its constituent amino acids (glutamyl, cysteine, and glycine). Of these, cysteine is almost always the limiting amino acid.

A particularly good source of dietary cysteine is whey protein, which has been shown to increase glutathione levels, with a wide variety of associated health benefits (US005451412A, www.glutathone.com)

Dietary alliums are a good source of cysteine, but their unpleasant side effects when consumed in other than small quantities limit their ability to serve as a primary source of cysteine. But allium-related compounds (e.g. garlic) can cause an increase in the reduced glutathione level by increasing the activity of the GSH reductase enzyme by up to 87% (ISBN0683181475, page 190), thereby increasing the proportion of GSH to GSSG. Dietary garlic or onion powder has been shown to increase the liver glutathione level in chickens by 40% (ISBN0683181475, page 190). And exposure to SAMC has been shown to significantly increase the total glutathione level of cells (CR61:725).

4.5.2 Amino Acid Degradation from Food Processing and Cooking

While whey protein is an excellent source of cysteine, its bioavailable cysteine is very sensitive to denaturation from heat or mechanical shock, requiring a microfiltration process to be used during its manufacture (US005451412A). If not prevented, this denaturation causes a significant decrease in the ability of whey protein to raise the glutathione level (US005451412A).

Other foods are also sensitive to protein loss due to denaturation. For example, oxidation reactions during manufacture can cut the protein content of apple juice by over 90%, as measured by electrophoresis (JAFC44:3413). The sulfhydryl and disulfide groups of proteins (i.e. the cysteine and cystine) are the most vulnerable amino acids to food processing and have been shown to be easily damaged by heat during cooking (N207:1269). Heating above 30 degrees C. causes progressive denaturation of cystine, and heating above 70 degrees C. causes progressive irreversible destruction of cysteine.

4.5.3 Intense Delivery of Cysteine

Normally, the primary source of cysteine is dietary protein, but in some cases it is desirable to supply more cysteine than can reasonably be supplied through the consumption of protein. For example, the standard treatment for acetaminophen (Tylenol®) poisoning (which causes severe glutathione depletion) is the oral administration of N-acetylcysteine (NAC). Of necessity, the NAC dosage is high (an initial dose of 140 mg/kg, followed by 17 doses of 70 mg/kg every 4 hours). The low toxicity of NAC, combined with its rapid conversion to cysteine (which in turn is rapidly converted to glutathione inside liver cells) is important for this application.

Pretreatment with 100 mg/kg of SAMC has been shown to protect mice from acetaminophen poisoning, suppressing the reduction in hepatic glutathione level after acetaminophen administration (PHYRES3:50). In this study, SAC, which is the other major component Aged Garlic Extract (AGE) was not nearly as effective. Post treatment with a single dose of SAMC (200 mg/kg) shortly after exposure to acetaminophen is also protective in mice (EJP433:177).

SAMC administration has been shown to be a very efficient way to deliver cysteine directly into cells. In vitro experiments show that when cells are exposed to SAMC (which contains a cysteinal radical that is easily converted to cysteine), the result is a significant increase in the total glutathione level of cells, even beyond the level that glutathione is normally regulated to (CR61:725).

4.6 Thiol-Disulfide Exchange Reactions

Thiol-disulfide exchange reactions are a unique feature of organosulfur chemistry that provide a rapid, reversible, energy-neutral, highly specific covalent reaction for bonding together (or separating) molecules that incorporate thiol or a disulfide bond (Torchinskii:1974).

More properly, this type of reaction should have been named the "thiolate-disulfide exchange reaction", because it always involves the ionized version of the thiol. If the thiol is represented as RSH, and the disulfide as R'S~SR" the exchange is as follows:

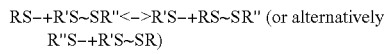

RS−+R'S~SR"<−>R'S−+RS~SR" (or alternatively R"S−+R'S~SR)

In other words, the ion and the disulfide form a temporary complex with three inter-reacting sulfur atoms (and an electron), which soon separates with the resulting thiolate ion coming from any of the three thiyl radicals and the remaining disulfide molecule containing the other two thiyl radicals.

This brief description is necessarily simplified. Exchange reactions can be subject to steric constraints. And the products of the reaction depend on the relative redox potentials of the three thiyl radicals. But to a first order, the reaction is rapid and the product mix is random, resulting in the formation of every possible mixed disulfide (and every possible thiol).

In practice, the reaction rate is pH dependent (due to the required ionization of the thiol). Also note that the total number of thiols is preserved (as is the total number of disulfide molecules). Only the mix has changed.

Thiol-disulfide reactions are important in the formation of the Cysteine-to-Cysteine bridges within proteins that help determine (and stabilize) the tertiary structure of the protein. They also are involved in the formation of Cysteine-to-Cysteine bridges between proteins.

Many enzymes have an "SH" group at their active site, and their activity depends on whether this remains an exposed thiol (or an exposed thiolate ion), with the enzyme being inactive if the thiol is "blocked" by an attached thiyl radical. This leads to the "redox regulation" of enzymes, which is an important mechanism for regulation, signaling, and control. Note that the inactivation of the enzyme is non-destructive, because a new thiol-disulfide exchange reaction between the blocked site and any thiolate ion that happens to float by can result in a disulfide floating away (leaving the SH group as a thiolate ion), and the enzyme becomes active again.

The majority of the organosulfur compounds that are discussed within this patent are thiols or disulfides, so exchange reactions are highly relevant to their associated chemistry.

4.7 The Pre-Hepatic Fate of the Organosulfur Compounds Derived from Garlic

While the shear number of garlic-derived organosulfur compounds can present a confusing if not bewildering variety, nevertheless when they are consumed they all are exposed to a gastric environment (and therefore to dietary cysteine) and to blood (during transport from the intestine to the liver). An in vitro study was performed (PM59:A688) to determine the likely reaction products in these environments. The results are given in Table 1 of PM59:A688 and are summarized here (Table I) for the compounds most pertinent to the present invention.

TABLE I

Reactions of organosulfur compounds in the presence of blood or cysteine

| | Reaction with Cysteine | | Reaction in Blood | |
|---|---|---|---|---|
| Compound | Half-life (min) | Product (moles) | Half-life (min) | Product (moles) |
| Allicin | <1 | SAMC (2) | <1 | AllylSH (1.6) |
| DADS | 45 | SAMC (1), | 60 | AllylSH (0.8) |
| SAMC | NR | | 3 | AllylSH (0.8) |
| AllylSH | 80 | SAMC (0.8) | NR | |

These results show that regardless of the compound which is consumed, SAMC can be formed as an intermediate reaction product and AllylSH as the final product in blood. This has led to the recommendation that in vivo or in vitro studies on the mechanism of action of these compounds should not use the parent compound, but rather should use AllylSH or possibly a metabolite of AllylSH (ISBN0683181475, page 214).

4.8 The Prevention and Treatment of Bacterial Infection.

In practice, the prevention of most bacterial infections is due to improved sanitary conditions. Immunization is also effective, but most people are not immunized against bacteria (beyond their childhood immunizations) unless there is a specific threat (e.g. immunization of military personnel against anthrax).

Experiments investigating methods for the prevention of bacterial infection induced by radiation treatment have shown that depletion of glutathione results in bacterial translocation (escape from the gut), and that OTZ treatment (which produces glutathione) is protective (JSR65:165).

The treatment of most bacterial infections is through the administration of antibiotics (or commonly, the management of the symptoms). The overuse (and misuse) of antibiotics for minor infections is a concern because this leads to the formation of resistant strains, which can result in untreatable, major infections. The use of antibiotics can also temporarily eliminate the "good" bacteria in the intestine, which can lead to superinfection because the good bacteria are no longer present to eliminate the "bad" bacteria.

Garlic and allicin have been extensively tested by researchers as antibiotics. In a review of antimicrobial spices, garlic inhibited all of the 30 types of bacteria that were tested (QRB73:3). This means that many people are actually consuming this antibiotic as part of their diet without really thinking about it.

In a comparison of the effectiveness of 13 types of antibiotics against 13 types of bacteria, Garlic and Chloramphenicol tied as the most effective antibiotics (inhibiting 12/13 of the species), and they also had the highest activity (average zone of inhibition of 20 mm) (IJEB15:466). Interestingly, the one type of bacteria that garlic was not effective against (Ps. Aeruginosa) was not inhibited by any of the other antibiotics either.

Rather than listing all of the bacteria that have been tested (and all of the associated references!), a summary of the more notable ones and the conditions that they can cause is presented:

Causing Pneumonia:
 Staphylococcus aureus, Strep. Pyogenes, Klebsiella pneumonae, Bacillus anthracis
Causing Stomach or Urinary Tract Infections:
 Salmonella typhimurium, E. coli, E. faecalis, E. durans Causing Ulcers and Stomach Cancer:
  *Helicobacter pylori*
Causing Intestinal Gas After Legume Consumption:
  *Clostridium perfringens*

While most of these antibacterial tests were in vitro, in vivo tests have been equally impressive. For example (IJEB15:466), when 4 week old chickens were fed 1 ml of crude garlic extract daily, the count of viable gram-negative bacilli per gram of rectal content was reduced by approximately a factor of 1000.

Apparently the "good" lactobacteria have evolved a tolerance to intestinal garlic (FM29:348), because while it inhibits the "bad" bacteria (*streptococci, coliforms, e. coli, salmonellae*) by a large factor (100×) in mice, it inhibits the "good" lactobacteria by a much lower amount (10×).

While not listed in detail here, garlic and allicin have also been shown to be antimicrobial against many fungi, viruses, parasites, etc. (MI2:125, ISBN0683181475), which are alternative forms of infection that are also subject to treatment within the scope of the present invention.

4.9 The Prevention and Treatment of ARDS

ARDS is normally treated by attempting to restore the lung's capacity for oxygen intake and by attempting to suppress the host's immune response. Most patients are of necessity treated after the development of ARDS (AJLCMP265:L501). Mortality rates are on the order of 50% (C111;1306)

Mechanical ventilation (hyperbaric oxygen) produces mixed results, in part due to the formation of reactive oxygen species (ROS). The percentage of oxygen content that was used in the past was too high, especially given that the sensitivity to oxidative damage can be heightened in the conditions related to ARDS (e.g. acid aspiration (AJPLCMP278:L1240) or glutathione depletion).

Nitric Oxide (NO) administration (also via mechanical ventilation) produces mixed results, because although it both dilates blood vessels (good) it also can produce nitrogen-based ROS such as peroxinitrate (ONOO—) which are extremely damaging.

N-acetylcysteine (NAC) is a non-toxic prodrug that rapidly provides bioavailable cysteine and has produced beneficial results in treatment of ARDS in some tests (C112:164), inconclusive results in others, and may be detrimental at high dosages (VASP39:247). NAC is normally administered orally or intravenously, although occasionally intraparietal administration has been reported.

NAC has multiple beneficial effects, starting with the prevention of glutathione (GSH) depletion. Lowered levels of GSH increase neutrophil adhesion to endothelial cells (the first event in the lung that can lead to the development of ARDS). Interestingly, this is due to an increase in the adhesion molecules on the surface of endothelial cells, rather than a change in the neutrophils themselves (CIRCUL84:516).

Neutrophil influx into lung lavages is induced by interleukin 1alpha (IL-1), but this is inhibited by intravenous NAC administration (150 mg/kg), presumably due to GSH (or NAC itself) scavenging oxidants such as $H_2O_2$, HOCl and *OH (AJPLCMP265:L501).

The generation of the cytokine-induced neutrophil chemoattractants which affect neutrophil migration is induced by NF-kB, which in turn is responsive the oxidative stress associated with GSH depletion. NAC treatment has been shown to decrease NF-kB activation, which in turn decreases neutrophilic inflammation in the lung (JI157:1630). Glutathione depletion also decreases the chemoattractive activity at the site of inflammation and can result in the improper migration of neutrophils to the lung in response to infections elsewhere (JID185:1115). Simultaneously, the decreased migration to the site of infection increases bacterial load and mortality. The antioxidant effect of NAC treatment markedly improves the survival of septic mice by simultaneously inhibiting inflammation while potentiating the host's innate immunity mechanisms.

NAC also increases mucus secretion, expectoration, and flow (in part due to its ability to increase cialary beat frequency (ARZN28:250), although high NAC concentrations (beyond $10^{-9}$ g/ml) suppress the cialary beat frequency and mucus flow (another reason not to use excessive NAC when treating ARDS).

OTZ (another prodrug that increases cysteine levels) has also been shown to be beneficial (C112:164), with the low toxicity of NAC (and OTZ) allowing high dosages to be used (e.g. over 10,000 mg/day for a 50 kg person).

Lung surfactant is comprised of phospholipids that reduce surface tension and greatly reduce the work of breathing. Surfactant replacement therapy, using either synthetic surfactant or calf's lung surfactant has shown some benefit in animal models, and shows promise in human trials PRR3:308), although it can exacerbate influenza infection (ICM27:1699). An increase in the surface tension of surfactant (which correlates with lowered concentrations surfactant-associated proteins) is an accurate early indicator of ARDS prognosis (AJRCCM160:1843). Those patients with high concentrations do not progress to ARDS, and those with low concentrations will have a high mortality rate (those in the middle are in the middle). It has recently been shown that surfactant protein A (the most abundant one) is easily damaged by the oxidants such as nitrite ($NO_2-$), peroxynitrite (ONOO—, generated from *$O_2$-and *NO), and hydrogen peroxide ($H_2O_2$), which are generated by activated neutrophils and other immune system cells during inflammation (FRBM33:1703).

Immune suppression through the use corticosteroid treatment also has had mixed results, but tends to be beneficial. Although the magnitude of the initial inflammatory response sets the pace for the evolution of ARDS, even patients with late ARDS and a low likelihood of survival can still benefit from the initiation of corticosteroid rescue treatment (C108:1315). But in many cases the response to corticosteroid rescue treatment is insufficient to protect the host and the excessive immune response remains more pathogenic than the infection. "The (poor) response to (corticosteroid rescue treatment) provides supporting evidence that ARDS patients most likely die with, rather than of, infection" (C111;1306).

Another form of treatment for ARDS that has been shown to give consistently beneficial results is supplementation with activated protein C, which has antithrombic, anti-inflammatory, and profibrinolytic effects (NEJM344:699).

It is interesting to note that garlic has also been shown to combine these effects (IJEB34:634). The amazing benefit of this was recently demonstrated in a study that utilized timed-release garlic powder tablets (Allicor, 300 mg/day). In a double-blind placebo controlled random 5-month trial in 42 children aged 10-12 years in comparison with 41 placebo-treated children, the incidence of acute respiratory viral infections in children was significantly reduced (PMID12718222). The mortality was reduced 1.7-fold, and the "health index" was 1.5-fold higher compared to the placebo treated group. In another study (using a dosage 600 mg/day), 172 children aged 7-16 years were compared to 468 controls. In this study, the morbidity was reduced 2.4-fold as compared to the controls. Their conclusion is that allicor tablets are effective for nonspecific prevention of acute respiratory infection in children and has no side effects. Note that the maximum allicin yield from the 600 mg of tablets is 2.4 mg, so even the higher dosage was small compared to the dosages required by other means of treatment.

5. SUMMARY OF THE INVENTION

The present invention provides a method for enhancing the overall beneficial immune system response in a host that works in conjunction with the host's natural immune system response to simultaneously enhance the host's ability to eliminate infectious microbes while suppressing the toxicity to the host of the immune system response.

The invention utilizes the non-enzymatic formation of allicin in response to the localized generation of H2O2 by immune system cells (such as neutrophils) to simultaneously increase the antimicrobial effect while reducing the cytotoxicity to the host. It is an advantage of the invention that it is able to nondestructively inhibit enzymes that would not normally be sensitive to deactivation by a thiol-disulfide exchange reaction. This results in part from the recognition that deactivation of SH dependant enzymes by allicin does not take place by the previously attributed mechanism of thiol-disulfide exchange reactions.

Briefly, in one of its aspects the invention calls for administering to a host an effective amount of an allium-related organosulfur compound such that a localized thiosulfinate is caused to be non-enzymatically formed in response to localized generation of H2O2 by the activated immune system cells.

It is shown that allicin, cysteine, and related organosulfur compounds have a variety of antimicrobial and immunomodulatory properties that work together with the host's immune system in the prevention and treatment of disease. The invention provides for simultaneous delivery of allicin, cysteine and related organosulfur compounds in an efficient manner, through the use of protein-bound S-AllylMercapto-Cysteine (SAMC) or similar prodrugs. The use of prodrugs avoids a variety of difficulties associated with the direct delivery of allicin or cysteine themselves.

The present invention can also utilize the enzymatic formation of allicin in the liver which provides a more uniform concentration over time (e.g. timed release) than the more conventional approach of using the enzyme alliinase to form the allicin during digestion.

A variety of illustrative modes of action are presented by which the invention may provide a beneficial combination of antimicrobial and anti-inflammatory modes of action.

The invention is also suitable for continuous preventative use in nutraceutical form, providing general health benefits while protecting from infectious diseases. Widespread use could provide "herd immunity", increasing the protection of the general population.

The preferred embodiments are "low tech", utilizing inexpensive ingredients and a simple manufacturing process, facilitating their widespread manufacture and use by economically disadvantaged groups.

The inventor has realized that there is a mechanism that can be utilized for the localized production of allicin in response to the host's localized generation of H2O2. It has been experimentally determined that the rate of allicin production from H2O2 is a non-linear function of the local H2O2 concentration, further enhancing the localization of the allicin production.

The inventor has also discovered that the mechanism of deactivation of many SH dependant enzymes by allicin is not by the previously attributed mechanism of thiol-disulfide exchange reactions, although in many ways the result is the same, and that allicin is able to nondestructively inhibit enzymes that would not be sensitive to deactivation by a thiol-disulfide exchange reaction.

The inventor has also discovered and developed new ways to formulate allium related compounds that have various advantages over existing dietary, dietary supplement, and medicinal products. These formulations may be utilized with the present invention.

Other aspects, advantages, and novel features of the invention are described below or will be readily apparent to those skilled in the art from the following specifications and drawings of illustrative embodiments.

6. BRIEF DESCRIPTION OF THE DRAWINGS

7. DETAILED DESCRIPTION OF THE ILLUSTRATIVE EMBODIMENTS

The antimicrobial aspects of the invention are presented using various bacteria that can cause pneumonia as the prototypical infectious agents. Then the immunomodulatory aspects of the invention are presented, using Acute Respiratory Distress Syndrome (ARDS) as the prototypical pathogenic immune system response. A specific example is then introduced in which the various potential modes of action are illustrated with respect to the known characteristics of a single disease, Severe Acute Respiratory Distress Syndrome (SARS). Preliminary to these examples, a discussion of the localized production of allicin in the presence of the host's activated immune system cells is presented.

7.1 Localized Production of Allicin from AllylSH and/or DADS

Thiols are known to have various antioxidant properties, including the ability to scavenge (H2O2), although the specific ability of allyl mercaptan in this regard may not have been previously investigated. It has been experimentally determined that allyl mercaptan (AllylSH) can reduce hydrogen peroxide (H2O2), oxidizing the AllylSH to diallyl disulfide (DADS, DAS2 in the figure) in the process (FIG. 1, initial concentrations of 10 mM H2O2 and 0.85 mM Allyl-SH)

Figure 2:
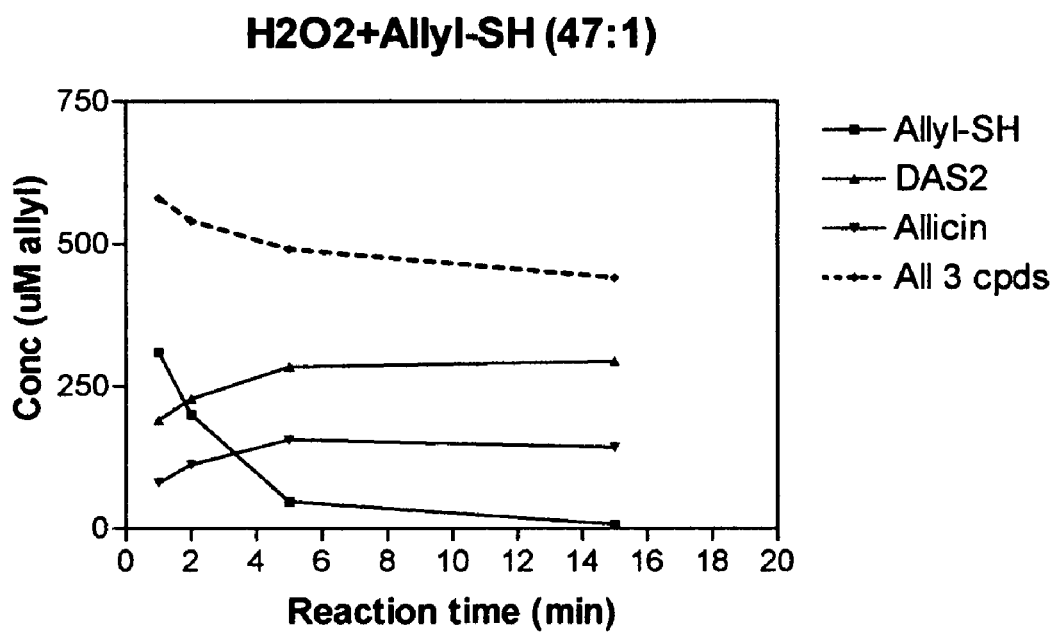
FIG. 2 shows the reduction of H2O2 by AllylSH and the further oxidation of diallyl-disulfide to allicin in the presence of high H2O2 concentrations.

Surprisingly, at high concentrations of H2O2, the DADS was found to be further oxidized to Allicin (FIG. 2, initial concentrations 40 mM H2O2 and 0.85 mM Allyl-SH). Previously, allicin has only been known to form when the intermediate, sulfenic acid (allyl-S—OH) is first formed, as is the case when allinase acts upon allin.

For convenience, the relevant chemical formulas are repeated below:

$$CH_2=CH\sim CH_2\sim SH$$

(AllylSH)

$$CH_2=CH\sim CH_2\sim S\sim S\sim CH_2\sim CH=CH_2$$

(DADS)

$$CH_2=CH\sim CH_2\sim S\sim S\sim CH_2\sim CH=CH_2$$
$$\|$$
$$O$$

(allicin)

While not wanting to be bound to a particular theory, the following reaction mechanism is proposed for the production of DADS from AllylSH in the presence of H2O2:

AllylS—+$H_2O_2$->AllylSO—+$H_2O$

AllylSO—+AllylSH->DADS+OH—

While not wanting to be bound to a particular theory, the following reaction mechanism is proposed for the production of allicin from DADS in the presence of H2O2:

DADS+AllylSO—->allicin+AllylS—

According to this theory, because both the formation of DADS and the formation of allicin are dependent on the concentration of AllylSO—, which in turn is dependent on the concentration of H2O2, the resulting allicin concentration is a strong function of the H2O2 concentration. Therefore, any H2O2 concentration gradient produces a stronger gradient of allicin formation, and the localization of allicin formation is a strong function of the localization of H2O2 concentration.

Figure 1:
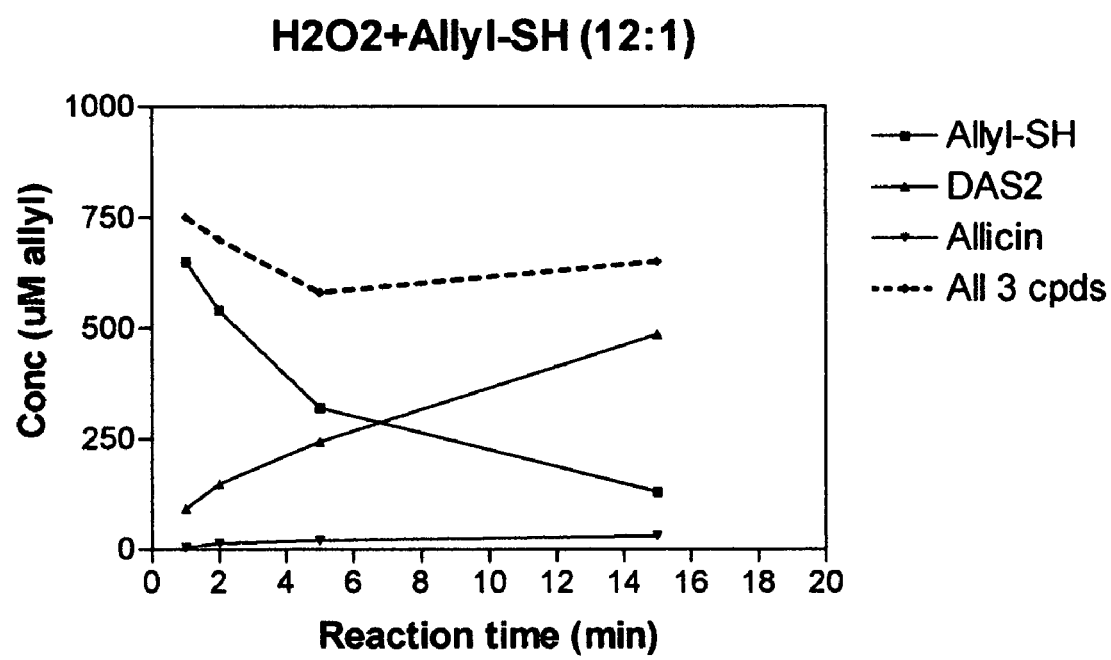
FIG. 1 shows the reduction of H2O2 by AllylSH, resulting in the non-enzymatic formation of diallyl-disulfide in the presence low H2O2 concentrations.

The two H2O2 concentrations illustrated in FIGS. 1 and 2 are respectively representative of the environment non-local to an activated neutraphil (FIG. 1, 10 mM H2O2) and to the localized environment (within approximately 10 cell distances) adjacent to an activated neutrophil that is generating reactive oxygen species (ROS) (FIG. 2, 40 mM).

The neutrophil has an amazing ability to generate H2O2, as is indicated by experimental evidence (e.g. JBC259:399 "Quantitative and Temporal Characteristics of Extracellular H2O2 Pool Generated by Human Neutrophils"). Even when diluted in saline solution by approximately a factor of ten thousand (a diluted concentration of $3\times10^5$/ml vs an estimated packed cell density of ~$3\times10^9$/ml), the H2O2 concentration produced by stimulated neutrophils reaches 12 uM. This corresponds to an undiluted H2O2 concentration of 120 mM. (Note that a dilution of a factor of ten thousand corresponds to a linear separation distance between the neutrophils of slightly over 20 cell diameters.)

The neutrophil is presented here as a prototypical type of cell that can generate extracellular ROS, but various other types of cells can also generate extracellular ROS (including not only cells of the immune system but also even some "normal" cells that can participate in an immune system response when activated). It will be appreciated that the various organosulfur compounds delivered to a host in accord with the invention may be effective in the environment of all such extracellular ROS generating cells, so that the invention may be applied beyond neutrophil cells alone.

7.1.1 Antioxidant vs Pro-oxidant Properties of Garlic and Allicin Explained.

Garlic and allicin have antioxidant properties because they are quickly metabolized to allyl mercaptan (allylSH), which has the same antioxidant properties as any thiol, including the ability to detoxify most forms of reactive oxygen and reactive nitrogen.

Garlic and allicin have pro-oxidant properties because the oxygen atom of the allicin molecule makes it somewhat unstable and capable of producing reactive oxygen through various reaction mechanisms. In particular, the reaction with cysteine produces as an intermediate product the sulfenic acid AllylSOH, which is so reactive that it is unlikely to be observed (see below).

The localized production of allicin from allylSH (via DADS) when exposed to a high concentration of H2O2 allows the antioxidant species to be distributed everywhere in the body and the pro-oxidant species only to be co-located with an attacking immune cell such as a neutrophil attacking an adjacent bacterium.

As will be shown below, this converts the non-specific cytotoxic agent H2O2 (generated by the neutrophil) to the more specific antimicrobial agent allicin.

In other words, by providing antioxidant protection almost everywhere, and a more specific antimicrobial agent just where it is needed, the "selective killing index" of the natural immune system response is significantly increased beyond that of the innate immune system.

7.2 Enzyme Inactivation by Allicin is by a Thiol-Thiosulfinate Reaction

The rapid reaction of allicin with cysteine (<1 minute half-life) that was reported in PM59:A688 is in surprising contrast to the slow reaction of DADS with cysetine (45 minute half-life) that they also report. (See TABLE I in section 4.7 above.) If the reaction mechanisms both proceed by a thiol-disulfide exchange reaction, both reaction rates would be expected to be similar and to be rate-limited primarily by the concentration of CyS— ions.

At a pH of approximately 7, only approximately 3% of the cysteine is ionized (the pKa of Cys is 8.53). It is interesting to note that the ratio of the half-life of allicin (say, 0.5 minutes) to the half-life of DADS (45 minutes) is also of the same order of magnitude. This led the inventor to investigate whether the reaction with allicin could involve un-ionized cysteine directly, and therefore not be a thiol-disulfide exchange reaction. Because the concentration of un-ionized cysteine is approximately 30 times that of Cys-, this suggested an explanation for why allicin reacts so much faster than DADS.

Although the reaction of allicin with cysteine has been well established (and was first reported by Cavalitto in 1944 (JACS66:1952), no detailed investigation appears to have been performed prior to the investigation of the reaction of allicin with glutathione (which contains cysteine) by Miron et al (WO:01/36450). These results were very interesting.

First of all, they conclude that the forward reaction is:

2 GSH+Allicin->2 AllylS~SG+$H_2O$

They named AllylS~SG "S-Allylmercaptoglutathione" because it consists of the mixed disulfide of allyl mercaptan and glutathione.

The present inventor's reasoned attempt: at a reaction mechanism yielded:

Allicin+GSH->AllylS~SG+AllylSOH (oxygenated AllylSH)　　　1

AllylSOH+GSH->AllylS~SG+$H_2O$　　　2

Miron et al (WO:01/36450) also have shown that the reaction rate has a strong dependence on pH over the pH range of 5 to 7 and concluded that this indicates that the glutathione is in the form of a mercaptide ion (GS—). But the required participation of a mercaptide ion in the reaction is inconsistent with the hypothesis that the present inventor's had formed that reaction with allicin could involve un-ionized cysteine directly. It was also inconsistent with the forward reaction mechanism advanced in the present disclosure.

The present inventor however has found a different explanation, not previously appreciated, for this pH dependence. Glutathione can convert to a thiazoline form (eliminating a water molecule in the process) at low pH (or even medium-low pH), and then it is no longer a thiol at all! (GAS1953, pages 21-29). At low pH, the infrared absorption spectrum clearly shows the absence of any cysteinal moiety and the establishment of the characteristic thiazoline peak at 2610 angstroms (GAS1953, page 24). The pKa of this transformation is 5.3 which, means that the transition between forms occurs gradually within the pH range of 5 to 7 (GAS1953, page 29), thus offering an alternative explanation of the pH dependence that is reported in WO:01/36450.

Confirmation of the feasibility of the reaction not involving any GS— ions was eventually achieved when the present inventor found a description of the reaction of S-monoxides (thiosulfinates) with thiols yielding mixed disulfides (Torchinskii:1974, page 95):

Substituting R=Allyl and R'SH=GSH yields the desired overall reaction.

Thus, the rapid reaction of allicin relative to diallyl disulfide has now been explained. It is a thiol-thiosulfinate reaction, not a thiol-disulfide reaction.

7.3 Example Benefits of the Invention

Many of the beneficial effects of the present invention are ultimately related either to the ability of the associated organosulfur compounds to form allicin, to participate in exchange reactions, to perform antioxidant functions, to inhibit (or activate) enzymes, or to enhance glutathione activity. These have been extensively described during the preceding sections. But the manifestations of these benefits are varied, as will be illustrated by examples of the multitude of potential modes of beneficial action against a specific disease (SARS) and its complication (ARDS).

7.3.1 Benefits of the Invention for the Prevention and Treatment of ARDS

ARDS is prototypical of conditions involving intense immune system responses that can be pathological. ARDS-like diseases that are addressed by the present invention include Acute Lung Injury (ALI), Systemic Inflammatory Response Syndrome (SIRS), Sepsis, Shock, Multiple Organ Dysfunction Syndrome (MODS), Compensatory Anti-inflammatory Response Syndrome (CARS), Mixed Antagonists Response Syndrome (MARS), and others.

Many of the effects that have been attributed to allicin probably involve other intermediates in vivo. As has been discussed above, dietary allicin or digestive allicin formation does not directly result in systemic availability of allicin. But the dietary consumption of other compounds containing allylmercapto groups can produce allicin in vivo via the formation of DADS and its subsequent oxygenation.

7.3.1.1 Immunomodulatory Effects and Benefits

Neutrophils are representative of cells that can produce extracellular ROS in an attempt to damage nearby microbes. The following discussion is intended to apply in part to all other cell types with this ability, including other forms of polymorphonuclear leukocytes, mononuclear phagocytes, large granular lymphocytes, "killer cells", and "normal" cells that can generate inflammatory extracellular ROS.

The initial onset of ARDS is extremely rapid, with significant damage to the lungs even in the first 15 minutes. The initial event seems to be the "sequestering" of neutrophils in small capilaries (some get stuck, causing a back up of even more) (COCC7:1). There is evidence that this in turn is initiated by intracellular signaling molecules (cytokines) generated by the inflammatory response to infection (C111:1306).

Enhancement of the endothelial NO Synthase enzyme (eNOS) is beneficial because its primary effect is circulatory dilation. But the enhancement of the inducible nitric oxide synthase enzyme (iNOS) in immune cells (such as neutrophils) is counterproductive in ARDS because its primary effect is the formation of ROS (BMCCD2:2). Therefore, inhibition of the iNOS is protective (A139:333). Allicin (or its metabolites, in this example and in those below) has been shown to enhance eNOS activity while simultaneously inhibiting iNOS. Other garlic components also have this effect (BST23:S136, FRBM30:747).

Another means of limiting inflammation is the inhibition of prostaglandin synthesis, which some allium related compounds have been shown to do amazingly well (diallyl disulfide at 50 uM/L produces 69% inhibition of prostaglandin synthase)(PM53:305).

ROS emitted by cells can cause nearby cells to also produce ROS, which can create a destructive feedback cycle (ISBN1573312851:327).

When ROS is generated by immune system cell to intentionally damage an adjacent infectious cell, the selective effectiveness of this process is dependant on the mean free path (lifetime) of the ROS until it either damages the intended victim, is scavenged by an antioxidant, or damages a host cell. Ideally, to avoid damage to other cells the mean free path would be on the order of one cell diameter. Therefore, in the presence of sufficient antioxidants, the likelihood of damaging a cell other than the intended one is low. But in the absence of antioxidants, the mean free path can extend to endanger many more nearby cells.

The antioxidant effects of compounds such as allyl mercaptan, other thiols, and even disulfides like diallyl disulfide (which now has been shown to reduce H2O2 when the H2O2 concentration is high) serve to limit the destructive range of ROS that diffuses away from its point of generation without significantly affecting the ability of neutrophils to damage microbes that are immediately adjacent.

Normally, the primary defense from H2O2 damage is provided by the enzymes catalase and glutathione peroxidase (PHRE59:527). But catalase saturates when the H2O2 concentration is high, so it provides limited or no protection adjacent to an active neutrophil. Glutathione peroxidase requires the involvement of glutatathione and produces GSSG which in turn must be reduced back to GSH by glutathione reductase, so after some initial protection it is also likely to saturate. This means that the availability of nonenzymatic antioxidant protection may be more important than would otherwise be expected.

The ability of allyl mercaptan and diallyl disulfide to produce allicin in the presence of high concentrations of H2O2 converts this non-specific oxidant which can produce a wide range of toxicities (and is implicated in the formation of a variety of more potent oxidants, such as the extremely reactive hydroxyl radical, *OH) to a much more specific and selective oxidant that is able to inhibit critical microbial enzymes, but has low toxicity to host cells.

The various properties attributed to NAC that are useful for the prevention and treatment of ARDS (see section 4.9 above) can also reasonably be expected to be properties of SAMC. Most of the effects from NAC treatment relate to the ability of NAC to serve as a prodrug for cysteine or are attributed to the antioxidant properties of NAC due to its being a thiol. Like NAC, SAMC produces cysteine in vivo, which is available for glutathione synthesis and as an antioxidant. SAMC also produces allyl mercaptan, which provides an additional thiol antioxidant beyond that provided by NAC.

7.3.1.2 Physiological Effects and Benefits

Allicin enhances endothelial NO Synthase enzyme (eNOS) activity (see above), and the resulting NO causes dilation of blood vessels, which should reduce the likelihood of neutrophils becoming stuck in capillaries. Allicin inhibits platelet aggregation, produces vasodilation, inhibits human neutrophil lysomal enzyme release, and promotes the maintenance of peripheral vasomotor tone (AA25:182). These effects may in turn be related to the inhibition of calcium uptake into platelets.

Allicin reduces platelet aggregation, which should also help keep the blood moving. Garlic has been shown to prevent hypoxic pulmonary hypertension in rats (AJP275: L283) which should be beneficial when ventilator assisted breathing is being used in ARDS treatment.

A comprehensive summary of the effects of garlic and related compounds on blood pressure, vascular resistance, and heart function is contained in ISBN0683181475:148. The responses in rats are also detailed in (JAP89:353).

Lactic acidosis is characteristic of all forms of shock, including ARDS (C111:1157), and hyperlactemia is a sensitive indicator of the onset of ARDS (C111:1301). Allicin inhibits human neutrophil lysomal enzyme release (AA25: 182), which may provide significant protection from this process.

7.3.2 A Detailed Example—Potential Modes of Action Against the SARS Coronavirus

While not intending to limit the scope of the present invention, its various benefits can be illustrated by its potential modes of action against the SARS coronavirus (or other viruses in the "coronavirus superfamily" which share many characteristics (ISBN0306445999:235)

7.3.2.1 Inhibition of Cell Fusion

Coronaviruses use spike proteins to fuse their viral envelope to the membrane of the cell that is about to become infected. The spike protein has a transmembrane anchor that is adjacent to a cysteine-rich domain. In the cysteine-rich domain, 9 of the 18 amino acids are cysteines (an extraordinary concentration of cysteines). It has been determined that even a small disruption to the pattern of the cysteines in this region will disrupt the fusion activity by 75% or more (i.e. it prevents the virus from attaching to the cell) (ISBN0306466341:205).

The entry of enveloped viruses into host cells first involves viral attachment to a specific cell-surface receptor in the endosome membrane, and then (for viruses with spike proteins) binding to a secondary receptor to allow fusion with the plasma membrane. For many viruses (including HIV) this involves a glycoprotein that is rich in disulfide bonds. On the supposition that this could involve disulfide bond formation with a free thiol group on the host cell, experiments were performed that showed that viral attachment can be prevented by the use of an SH blocking reagent (in effect, blocking access to the previously free thiol) (JGVI80:2861).

In other words, the attachment of the cysteine-rich domain of the viral spike protein to the host cell would be disrupted if something else is already attached to the previously exposed end of the cysteine. In the context of the present invention, if the exposed cysteine is ionized (i.e. S—) this could easily be produced by a thiol-disulfide exchange reaction between an SAMC molecule floating by, which could leave an allyl mercapto radical attached to the viral cysteine (while the cysteine portion of the former SAMC molecule floats away).

Conversely, if the exposed cysteine is not ionized (i.e. SH), a disulfide will not be able to participate in an exchange reaction with it, but a thiosulfinate (such as allicin) would be able to participate in a thiol-thiosulfinate exchange reaction, leaving an allyl mercapto radical attached to the viral cysteine (while the sulfenic acids portion of the former allicin molecule floats away).

Finally, if pairs of cysteines on the spike protein are disulfide bonded together, a thiol (such as allyl mercaptan) could disrupt the disulfide bonds of cysteine-rich domain of the viral spike protein itself via a thiol-disulfide exchange reaction. This would leave the previously free thiol attached to one of the cysteines on the spike protein, blocking its attachment to the host cell.

If this mechanism for inhibition of cell fusion is significant in vivo, it would be expected that the severity of infection would depend on the prevalence of thiol and/or disulfide molecules floating around between the cells, which are known to decrease with the age of the individual (ISBN1573312851:350, ISBN01263666705:531). The antioxidant status of the individual in general also depends on age ((ISBN1573312851:350, ISBN1573312851:353). This correlates with the increased incidence of SARS disease with age (L03:4432, L03:4453), indicating that ingested SAMC (or an other thiyl radical containing compound) may be effective in the prevention and treatment of SARS.

In general, the prognosis of SARS in children is much better than the prognosis for adults (L03:4127), which is also consistent with this mode of action.

7.3.2.2 Inhibition of RNA Synthesis

Coronaviruses rely on RNA synthesis for their replication. Allicin has been shown to significantly reduce the activity of the enzymes involved in RNA synthesis (BBA1379:233), which could significantly reduce the viral replication rate. Measurement of the effect of allicin on the replication rate of cells (which also require RNA synthesis to replicate) shows that the rate can typically be cut in half (NC38:245).

For example, if the doubling time for the viral replication is one half hour, after 10 hours the virus would have doubled twenty times, and the viral load would increase by a factor of a million. But if the doubling time was increased to a hour by the consumption of allicin (or by the in vivo production of allicin from consumed SAMC), in 10 hours the virus would only have doubled ten times, producing a viral load increase of only 1024 times. Any slowing of the viral replication rate gives the person's immune system more time to fight the virus before a large viral load develops (and hopefully defeating the virus before then). For example, a slower replication rate gives the immune system the time that it takes to create specific antibodies for the current infection.

This indicates that ingestion of allicin (or another compound that can metabolize to allicin, such as SAMC) supports a mode of action that may be beneficial in the prophylactic prevention and therapeutic treatment of SARS.

7.3.2.3 Inhibition of Proteolytic Activity

Coronaviruses use a papain-like protein to generate essential viral proteins (ISBN0306466341:267, ISBN0306445999:227, ISBN0306459108:141, ISBN0306459108:173). The operation of the active site of this enzyme in coronaviruses is similar to that of other papain-like enzymes, so it is reasonable to assume that an inhibitor of papain would also inhibit this proteinase, thereby reducing the viability of the coronavirus.

Allicin has been shown to be extremely effective at inhibiting the activity of papain (BBA1379:233). This is impressively demonstrated by a figure that is published in the prior art (FIG. 6 of BBA1379:233which shows that excess allicin (0.06 mM) can almost completely inactivate papain activity, and that this inhibition can be rapidly reversed by excess glutathione.

7.3.2.4 Prevention of Oxidative Stress Induced Viral Replication

A variety of viruses (including influenza and HIV) have been shown to reduce the level of glutathione in lungs (ISBN08176229416:143). A dramatic example of this is shown by a figure in the prior art "intracellular glutathione content of AGMK cells infected with Sendai virus (Intracellular glutathione content of AGMK cells infected with Sendai virus" (FIG. 2.A in ISBN08176229416:143). This shows an example of viral infection rapidly depleting cellular glutathione (down to <10% at 10 minutes post infection and down to <3% at 20 minutes), then more gradually recovering back to 70% at 60 minutes.

To make matters worse, various viruses (including HIV) have been shown to have an increased replication rate during oxidative stress (e.g. when the GSH level is reduced) (ISBN08176229416:143). Thus, preventing the oxidative stress can inhibit viral replication. A dramatic example of this is shown by a figure in the prior art "Effect of addition of exogenous GSH on intracellular glutathione levels and on viral infection" (FIG. 2.B in ISBN08176229416:143). This shows that either pretreatment with glutathione or post treatment (one hour after infection) dramatically reduces the level of infection (by 95% in the case of post treatment) when measured 24 hours post infection.

The immune response itself naturally creates oxidative stress because reactive oxygen species (ROS) are generated by cells (such as activated macrophages) in order to destroy adjacent infective material. These ROS can also damage the adjacent cells of the host, giving rise to inflammation. Various antioxidants, including glutathione, limit the propagation of the ROS, and thereby reduce the level of immune response related oxidative stress.

The rate of viral replication of the SARS virus may be influenced by the level of oxidative stress, in which case the antioxidant properties of allyl mercaptan, SAMC, and GSH support a mode of action may be beneficial in the prevention and treatment of SARS.

7.3.2.5 Prevention of Concurrent Infection by Influenza

The possibility of a recombination of influenza RNA into coronavirus RNA is especially dangerous (ISBN0306436647:367). The ability of allicin to inhibit the influenza virus (PM51:460) decreases the probability of simultaneous infection.

7.3.2.6 Reduction of Damage from Immune Response Induced Inflammation.

The impaired lung function induced by SARS has been attributed to be primarily due to the immune response of the host rather than from the virus itself. "Pathology studies show that the principal cause of the damage is not the SARS agent but the body's immune reaction against it", (New York Times, Apr. 12, 2003).

This is in common with another related virus that causes porcine respiratory disease (ISBN0306459108:593), and consistent with the results for severe pneumonia reported in (T55:46).

In an attempt to prevent this steroids have been administered (to suppress the body's immune response) for the treatment of SARS, with only partial success.

The antiviral ribaviron is also believed by some hospitals to be beneficial in treating SARS, even though the CDC claims that it does not inhibit SARS replication. However, there are other mechanisms by which ribaviron could be providing protection from ARDS. In addition to being antiviral, ribaviron is known to significantly inhibit the replication of T and B lymphocyte cells (clue to its inhibition of nucleotide synthesis) thereby decreasing the intensity of immune system response (AAC22:108).

This is especially interesting because the damaged lungs show a surprisingly low level of virus (New York Times, Apr. 12, 2003), implying that the replication rate of the virus in lungs may naturally be lower than the rate of formation of immune response cells. Hence the lack of nucleotides induced by ribaviron may not affect the viral replication (whose rate is slow) as much as it affects the formation of immune cells (which would normally be rapid when fighting disease).

In any case, a downside of suppressed immune system response can be an increased probability of reinfection. An alternate method for reducing immune system induced lung damage is not to inhibit the formation of immune response cells, but instead to limit the extent of the damage from the ROS that immune response cells produce. The antioxidant properties of allyl mercaptan, SAMC, and glutathione can provide a protective mechanism that is an alternative to the immune response suppression by ribaviron.

7.3.3 Antiviral Assay in Progress

A submission of SAMC as an antiviral agent has been made to the US government's SARS screening program. Initial results using a moderate concentration (0.01 mM) showed a 6% reduction in the viability of infected cells with no toxicity to uninfected cells. These results were sufficiently promising that a second round of screening is now in progress, utilizing concentrations of 0.1 mM and 1.0 mm.

7.4 Protein-bound SAMC and Similar Prodrugs

Many of the properties of the relevant organosulfur compounds have been described above, but there are additional implementation-related considerations.

As explained above, suitable embodiments of organosulfur compounds must ultimately be able to form allicin, which means that they must be able to form DADS in vivo. In practice, this only requires that the selected compound include an allylmercapto group (AllylS) bound to the rest of the compound in a way that permits it to be freed during digestion. The simplest choices that meet this requirement are AllylSH, DADS, and allicin.

AllylSH has a stench that only a skunk could envy, which makes it commercially impractical. DADS has poor water solubility and has the taste and smell of garlic, which some people find objectionable, again making it less commercially desirable. Allicin has some toxicity, which limits the potential dosage. It can give a burning sensation as it reacts with tissue. And it also tastes and smells like garlic.

Another consideration is that these compounds are now known to form AllylSSG when expose to glutathione, which decreases the amount of free GSH in the cell. Due to the importance of glutathione, even a temporary depletion is undesirable, especially if a significant dosage is being used for the treatment of a disease in progress. This argues for the use of AllylSSG, because then as much glutathione is supplied as is being consumed.

But there is a simpler (and less expensive) way. AllylSSG provides little benefit over any other means of simultaneously delivering cysteine because GSH has been shown not to be transported into cells in its undigested form. (Even if it survived digestion, the cells would not absorb it.) So GSH (and by implication AllylSSG) is no more effective that any other source of dietary cysteine.

Figure 3:
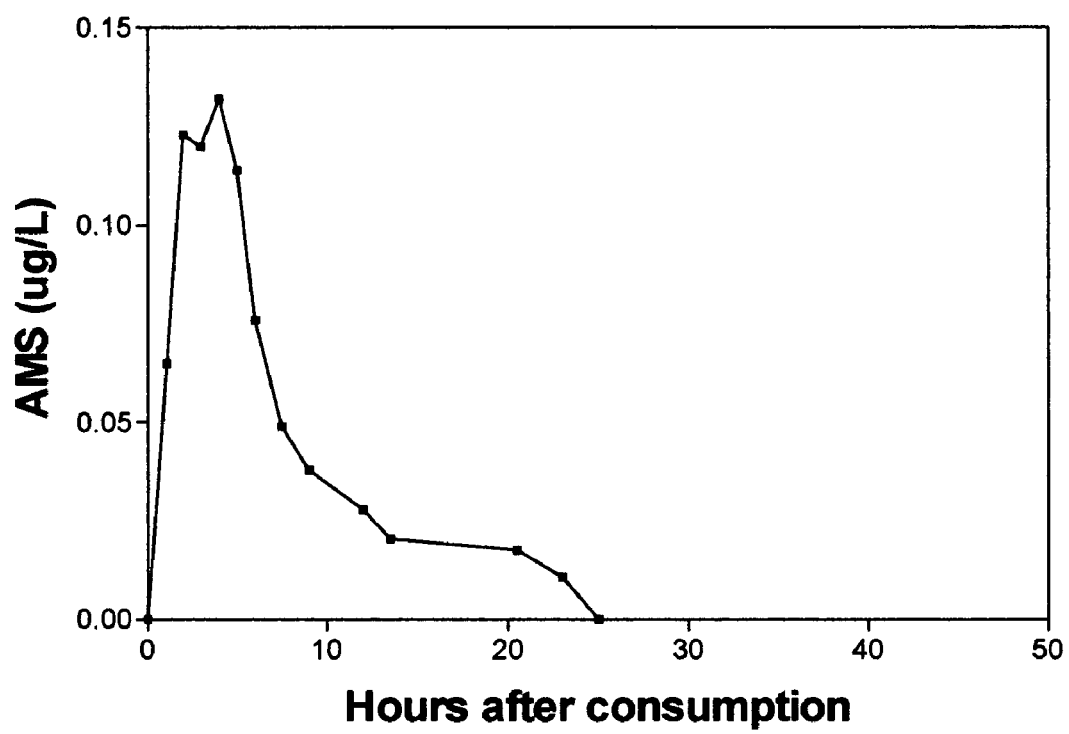
FIG. 3 shows the time profile of bioavailable allicin (as indicated by AMS in breath) provided by the prior art.

SAMC is a viable alternative to AllylSSG and is generally less expensive. And SAMC is a particularly versatile alternative. Via thiol-disulfide exchange reactions, the SAMC molecules can form AllylSH and cysteine molecules (primarily in reductive environments, such as intracellularly), and they can also form DADS and Cystine molecules (primarily in oxidative environments, such as extracellularly). In turn, the DADS can form allicin in the liver via cytochrome P450 (JN131: 1041S). This process occurs gradually, providing a form of "timed release", compared to allicin from garlic powder (See FIG. 3).

But SAMC still has the taste and smell of garlic. This may not be much of a commercial impediment since (for capsules at least) enteric coating can be used to eliminate the taste and smell, although it can sometimes be difficult to get the coating right.

In some sense the best (and least expensive) source of cysteine is dietary protein. In a patent application filed contemporaneously with the present application, the present inventor teaches the formation of protein-bound S-Allyl MercaptoCysteine (protein-bound SAMC) from foodstuffs and commercially available food additives. Such protein-bound SAMC is a preferred compound for use in the present invention.

Here are some examples of dietary administration of suitable organosulfur compounds.

EXAMPLE 1

An Apple Juice Composition to Provide Bioavailable Allicin

First prepare a 1/400 dilution of allyl mercaptan by adding 1.25 ml (a quarter teaspoon) of food grade allyl mercaptan to 500 ml of distilled water.

Food grade allyl mercaptan is available from a variety of sources, including Penta International Corporation, Livingston N.J., USA. The cost for a 100 ml bottle is approximately $400 (which is less than 1.5 cents per serving). In practice, the production cost is dominated by the price of the apple juice. Kosher grade is also available, as an option.

Interestingly, laboratory grade allyl mercaptan is available from LabDepot, Inc. (www.labdepotinc.com) for only $107.94 per 100 ml, but for this use the present inventor decided to utilize the food grade product (non-Kosher).

When the allyl mercaptan is added to the water, it initially floats on the surface because its solubility is only 1 in water (vs 5 in ethanol) and its density, at 0.925, makes it lighter than water. But if left overnight at room temperature, it will uniformly distribute in solution giving the liquid a slight milky color.

The best apple juice to use is one with minimal processing, but good results have been obtained with both filtered or Unfiltered, and pasteurized or not. The present inventor's preference is "Andronico's 100% Organic" from the local supermarket.

For the apple juice, add one teaspoon (5 ml) of diluted allyl mercaptan to each 8 fluid ounces of beverage and let it sit overnight. Shake before using.

The dosage (per 8 oz serving) is $1/400 \times 1$ g/ml$\times 0.925 \times 5$ ml=11.5 mg of allyl mercapton. This is roughly the theoretical equivalent in "total thioallyl content" to 13 mg of allicin, because allicin yields 2 AllylSH per molecule, and the ratio of their formula weights is 162.26/74.13=2.19. This is a reasonable dosage because human consumption is typically 10 mg/day among Americans who) eat fresh garlic (a 5-gram clove a day).

Figure 4:
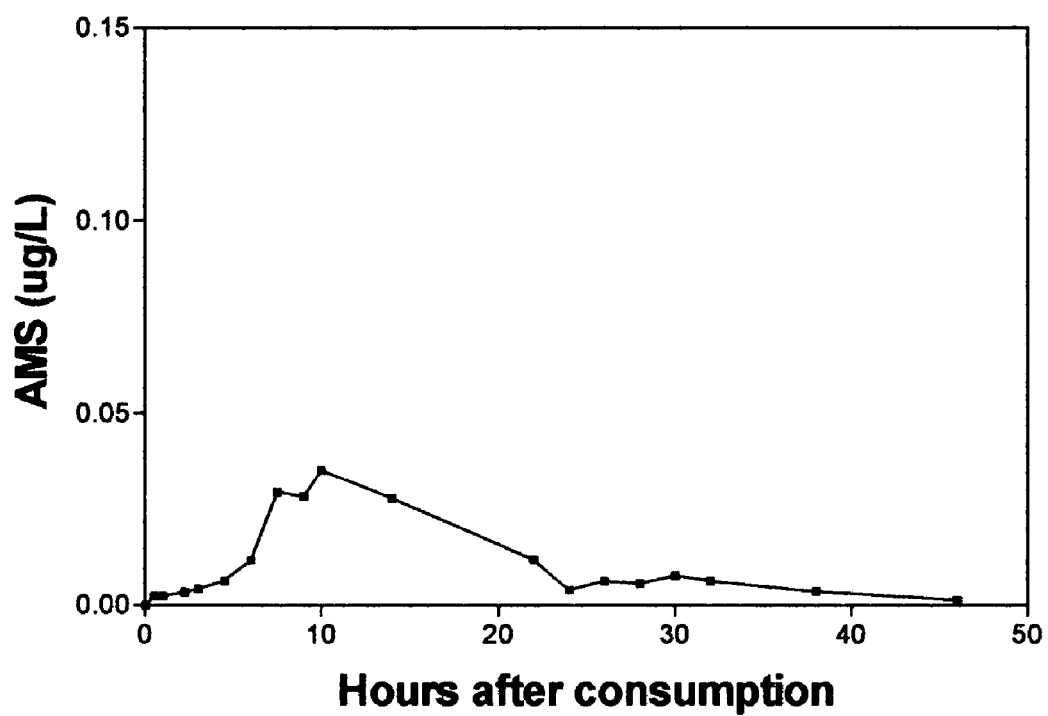
FIG. 4 shows the time profile of bioavailable allicin from an apple drink that contains protein-bound SAMC.

An "Allicin Equivalent Bioavailability Assay" of the apple drink was performed for the inventor by Plant Bioactives Research Institute. The resulting graph is shown in FIG. 4. In some ways the results were as expected:

1. AMS was detected (AllylMethylSulfde, a compound in the breath whose total volume has been shown to be proportional to the allicin-equivalent thioallyl content of a variety of garlic related compounds, including allicin, diallyl disulfide, allyl mercaptan, and SAMC).

2. There was a delay of several hours before the significant rise in AMS. This is probably due to the normal dietary delay in protein digestion (which is a step in the liberation of the protein-bound SAMC).

But unfortunately, the total volume of AMS was only about ⅕ of the amount that would be expected from the amount of SAMC that was intended to be produced. The reason for this discrepancy has not yet been determined. For now, it is being attributed to the difference in the digestive and/or metabolic pathway between protein bound SAMC and the other (non-bound) compounds. As presently understood, all of the allyl mercapto groups remain in the product up to the point of consumption, and this product (and the other products containing protein bound SAMC that have been consumed by the evaluators during the past year) seems to produce the biological response that would be expected (decrease in number of colds per year, thinning of saliva, . . . ). In comparison, this performance is no worse than the performance achieved by most garlic dietary supplements in the past (see the discussion above).

Figure 5:
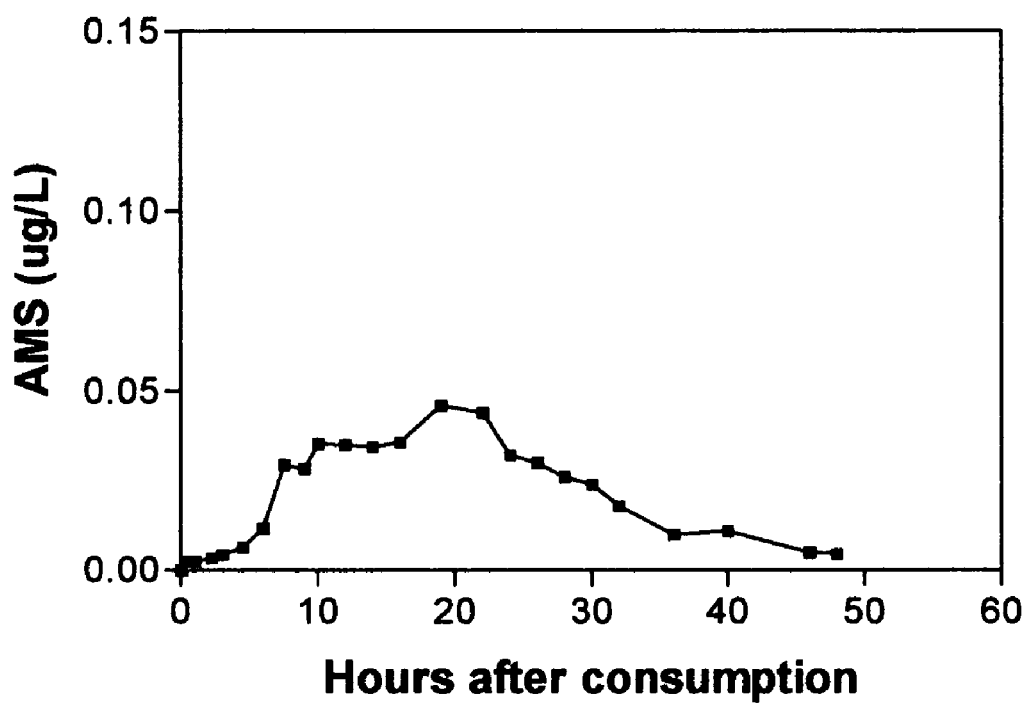
FIG. 5 is a superposition of the time profile of bioavailable allicin for the apple drink consumed twice a day.

Consumption of the apple juice twice a day (e.g. at 8 AM and 6 PM) provides a reasonably continuous level of allicin production, as is shown in FIG. 5.

EXAMPLE 2

A Dietary Supplement Capsule

The dietary supplement capsules are produced by mixing one cup (250 ml) of whey protein powder with one cup of 1/100 dilution allyl mercaptan in a blender for 30 seconds. Interestingly, even after this short interval, the resulting mixture tastes as milk-like as it does garlic-like. The mixture is pored into a non-stick baking pan and a stainless steel screen is placed on top.

After drying is completed (a couple of days), a spice grinder is used to produce a powder which is then put into capsules using the "Cap-M-Quik" assembly from CAP-M-Quik Corporation, Berry Creek Calif., USA. The yield is 250 capsules.

The calculated dosage is $1/100 \times 1$ g/ml$\times 0.925 \times 250$ ml$\times 1/250$=9.25 mg of allyl mercaptan per capsule. When expressed as an equivalent amount of SAMC (i.e. the "SAMC" portion of "protein bound SAMC"), this would be 24.12 mg of SAMC.

These are the capsules that I am currently taking, one a day (two during flu season). Various friends and relatives have also tried them (free of charge), and have typically reported that they "didn't get sick this flu season."

Figure 6:
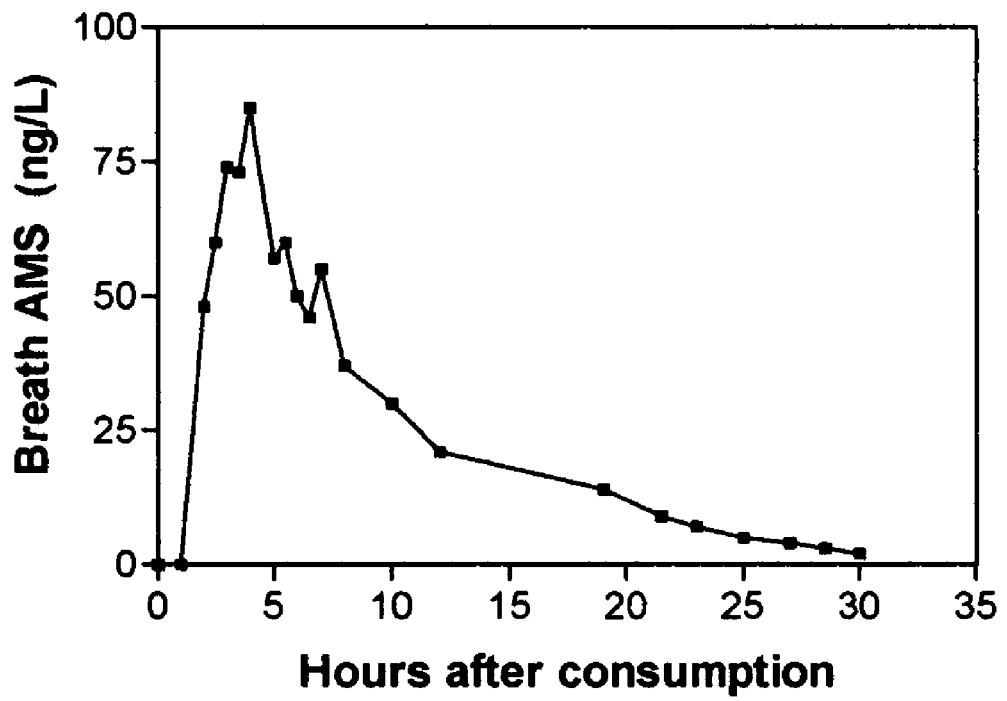
FIG. 6 shows the time profile of bioavailable allicin from a dietary supplement capsule that contains protein-bound SAMC.

The results of the bioavailability test for the capsule is shown in FIG. 6.

EXAMPLE 3

A Higher Dosage Capsule

Higher dosage capsules are produced by mixing the contents from eight L-cysteine 500 mg capsules (manufactured by Solgar Vitamin and Herb Company, Leona N.J., USA) with 15 ml of 1/10 dilution allyl mercaptan. The mixture is put into a non-stick container to dry.

After drying is completed (a couple of days), a mortar and pestle is used to produce a powder which is then put into capsules using the "Cap-M-Quik" assembly from CAP-M-Quik Corporation, Berry Creek Calif. The yield is 8 capsules.

The calculated dosage is $1/10 \times 1$ g/ml$\times 0.925 \times 15$ ml$\times 1/8 = 173$ mg of allyl mercapton per capsule.

These capsules have been consumed by the inventor occasionally with no unpleasant effects.

These examples are illustrative and the invention is not intended to be limited to these examples. The use of protein bound SAMC is convenient but not essential, and would not even be an acceptable means for some applications, such as for intravenous administration.

Novel preparations of the invention may be made by a number of conventional methods. Nutritional wafers are within the scope of the invention. Compositions for oral dosage can include inactive components which provide for easier or more pleasant oral administration. Oral compositions may also include other active ingredients.

Methods of administration include non-oral means such as topical ointments, nasal, sublingual, intravenous and parenteral or any other method that will present the active metabolites or their prodrugs to the cellular environment of the host. The host may be any type of animal with an immune system similar to that of a mammal.

7.5 Comparison with Aged Garlic Extract (AGE)

Previously, the only commercially available dietary supplement containing SAMC was Aged Garlic Extract from Kyolic Research (according to www.kyolic.com). The "AGE" product contains primarily the water-soluble compounds S-allylcysteine (SAC, 0.62 mg/g) and SAMC (0.14 mg/g), but it also contains lesser amounts of the lipid-soluble compounds diallyl sulfide, triallyl sulfide, and DADS.) Thus, even though it contains SAMC and other compounds, it predominantly consists of SAC. AGE contains no allicin (ISBN0683181475, page 104).

SAC contains a cysteinal radical bonded to an allyl group, with just one sulfur atom in the molecule. In contrast, SAMC contains a cysteinal radical bonded to an allyl-mercapto group, resulting in two sulfur atoms in the molecule (bonded together by a disulfide bond). Therefore SAMC can participate in disulfide exchange reactions, but SAC cannot. Also, via thiol-disulfide exchange reactions, an SAMC molecule can ultimately yield both a cysteine molecule and an allyl mercaptan molecule. In general, SAMC has more beneficial medicinal properties than SAC does.

The SAMC content of available dietary supplements is quite low compared to the range of concentrations that is provided by the present invention. The SAMC content of AGE is advertised as being 200 mcg/g, and AGE-containing dietary supplements typically contain less than 1000 mg of AGE, resulting in a maximum dosage of only 200 micrograms of SAMC per capsule. The present invention includes dosages of at least in the milligram range, typically on the order of up to 100 milligrams of SAMC per capsule, and can support dosages significantly beyond this, if such dosages are found to be beneficial. For example, SAMC dosages of up to 200 mg/kg have been used successfully in mice (EJP433: 177), which corresponds to a dosage of 14,000 mg for a person weighing 70 kg.

The effective amount of protein-bound SAMC for the compositions of the instant invention is in the range of 0.1 to 50 mg. This range for the dose of SAMC is equivalent to a range of 0.038 to 18.9 mg of allyl mercaptan, based on the stoichiometry and molecular weights of cysteine and allyl mercaptan.

7.6. Use of Other Allium Related Organosulfur Prodrugs.

The present invention has been illustrated according to the use of the allylmercapto radical and its subsequent conversion to other organosulfur compounds, such as the thiosulfinate allicin. But other mercapto radicals have been shown to participate in other thiosulfinates that have similar properties. For example, the thiosulfinates from onion tend to contain propyls instead of allyls. Just as the compound diallyl disulfide can be oxygenated to allicin, the onion-derived compounds di-n-proply disulfide and n-propyl allyl disulfide can be oxygenated to their corresponding thiosulfinates, which may explain their antibiotic effectiveness against *Salmonella typhimurium* and *E. coli* (AM17:903).

Similarly, the organosulfur compounds derived from cabbage tend to contain methyl groups, with methyl methanethiosulfinate (MMTSO) showing remarkable antimicrobial properties (JFP60:67).

A study of the nematicidal activity of various sulfur compounds from the plants "Allium grayi Regel" and "Allium fistulosum L. var. caespiitosum" concluded that those which have a disulfide, trisulfide, thiosulfinate, or thiosulfonate group are potential nematicides and antimicrobials (ABC52: 2383). The most effective compound found was the thiosulfinate $CH_3(CH_2)_2S\sim SO(CH_2)_2CH_3$.

In general, it is expected that mercapto radicals containing up to 5 carbon atoms in a linear or branched configuration, when disulfide bounced to cysteine, share many of the properties that are attributed to SAMC (and its derivatives). Studies of radioprotective substances have shown that thiol compounds with more than 5 carbon atoms are ineffective in protecting animals from radiation exposure. The explanation advanced here is that when thiols that are larger than this are consumed, they eventually form mixed disulfides with glutathione which are excreted from cells (and ultimately from the host).

SAMC has the advantage that it metabolizes to allyl mercaptan and other known derivatives of garlic that have been successfully consumed by millions of people. And its related organosulfur compounds (such as allicin) have been extensively investigated. The present invention, however, applies also to the more general class of compounds that have been presented in this section, which are referred to herein as "allium-related organosulfur" compounds.

The present invention has been illustrated according to its application in the prophylactic prevention and therapeutic treatment of infectious diseases and for the prophylactic prevention and therapeutic treatment of pathological immune system response, but given the benefit of this disclosure those skilled in the art will realize that it can also be applied to other conditions involving inflammation, such as chronic arthritis. Therefore, the invention is not to be limited to the above description and illustrations, but is defined by the appended claims.

What is claimed is:

1. A method of increasing the broad spectrum antimicrobial activity localized to the environment adjacent to activated immune system cells of a mammalian host currently emitting reactive oxygen species while reducing cytotoxicity of said antimicrobial activity to host cells, comprising:
  administering to a mammal in need of said antimicrobial activity a composition comprising one or more allium related organosulfur compounds consisting of a total of 0.1 to 50 milligrams of mercaptans disulfide bonded to cysteine residues; said cysteine residues being within protein molecules that contain cysteine and said mercaptans comprise one sulfur atom and up to 5 carbon atoms in a linear or branched configuration;
  wherein said one or more allium related organosulfur compounds metabolize within said host to form one or more mercaptans, said one or more mercaptans each comprising a sulfur atom and up to 5 carbon atoms in a linear or branched configuration;
  wherein said one or more mercaptans serve as an antioxidant within said host, the successive oxidation of said one or more mercaptans forming a thiosulfinate or mixed thiosulfinate resulting in a localized thiosulfinate or mixed thiosulfinate being non-enzymatically formed in response to the localized generation of reactive oxygen species by the activated immune system cells;
  wherein said localized thiosulfinate or mixed thiosulfinate is a broad spectrum antimicrobial agent;
  whereby the antimicrobial activity of the immune system cells that are currently emitting reactive oxygen species is increased by the formation of an additional antimicrobial agent.

2. The method of claim 1 wherein said thiosulfinate is allicin.

3. The method of claim 1 where said allium related organosulfur compound is protein-bound S-AllylMercaptoCysteine comprising:
  (a) dietary protein molecules modified to include bound allyl mercapto radicals;
  (b) said bound allyl mercapto radicals comprising said allyl mercapto radicals disulfide bonded to cysteine residues of said protein molecules.

4. The method of claim 1 where said reactive oxygen species is hydrogen peroxide.

5. An orally administrable protein based allium related composition for delivering both antioxidant and localized antimicrobial agents to increase the broad spectrum antimicrobial activity of the immune cells in a host in need thereof, said composition comprising:
  (a) protein molecules modified to include a total of 0.1 to 50 milligrams of cysteine bound mercapto radicals;
  (b) said cysteine bound mercapto radicals consisting of mercapto radicals disulfide bonded to cysteine residues of said protein molecules;
  (c) said mercapto radicals comprising one or more types of mercapto radicals each comprising a sulfur atom and up to 5 carbon atoms in a linear or branched configuration;
  (d) said cysteine bound mercapto radicals being metabolized via digestion or thiol-disulfide exchange reactions to form one or more mercaptans;
  (e) said mercaptans locally forming thiosulfinates or mixed thiosulfinates when oxidized by reactive oxygen species emitted by activated immune cells;
whereby antioxidant mercaptans are provided throughout the body of the host and the activated immune cells of the host have their antimicrobial activity increased.

6. The composition of claim 5 where said mercapto radical is the AllylMercapto radical.

7. The composition of claim 5 where said reactive oxygen species is hydrogen peroxide.

8. The composition of claim 5 in the form of a nutraceutical suitable for administration as a food to a host.

9. The composition of claim 8 where said protein is the protein of apple juice.

10. The composition of claim 5 in the form of a dietary supplement suitable for oral administration to a host.

11. The composition of claim 10 where said dose is in the form of a capsule.

12. The composition of claim 5 in the form of a drug.

13. A method of manufacturing an orally administerable protein based allium related composition for delivering both antioxidant and localized broad spectrum antimicrobial agents to increase the antimicrobial activity of the immune cells in a host in need thereof comprising:
  (a) mixing molecules of a protein which contains cysteine and mercaptan molecules in water, said mercaptan molecules comprising a sulfur atom and up to 5 carbon atoms in a linear or branched configuration;
  (b) drying the mixture in air;
  (c) grinding the dried mixture to form a powder;
  (d) filling capsules with said powder such that each of said capsules contains a total of 0.1 to 50 milligrams of said mercaptan molecules plus said cysteine residues disulfide bonded together.

14. The method of claim 13 where said protein molecules comprise whey protein and said mercaptan molecules comprise allyl mercaptan.

15. The method of claim 1 where said composition comprises a nutraceutical in the form of a beverage.

16. The method of claim 1 where said composition comprises a dietary supplement in the form of a capsule.

17. The method of claim 1 where said one or more mercaptans comprise allyl mercaptan.

18. The method of claim 1 where said one or more mercaptans comprise n-propyl mercaptan.

19. The method of claim 1 where said one or more mercaptans comprise methyl mercaptan.

20. The method of claim 1 where the composition comprises N-acetylcysteine and said one or more allium-related organosulfur compounds.

21. The method of claim 1 wherein said mammal is suffering from a microbial infection.

* * * * *